US012599388B2

(12) United States Patent
Budyansky et al.

(10) Patent No.: US 12,599,388 B2
(45) Date of Patent: Apr. 14, 2026

(54) BONE GRAFT DELIVERY DEVICES AND METHOD

(71) Applicant: Zimmer, Inc., Warsaw, IN (US)

(72) Inventors: Maxim Budyansky, Baltimore, MD (US); Marton Varady, Farmington, CT (US); George Andrews, Farmington, CT (US); Thomas San Giovanni, Farmington, CT (US); Giselle Cabada, Farmington, CT (US); Neil Shah, Baltimore, MD (US)

(73) Assignee: Zimmer, Inc., Warsaw, IN (US)

( * ) Notice: Subject to any disclaimer, the term of this patent is extended or adjusted under 35 U.S.C. 154(b) by 89 days.

(21) Appl. No.: 18/398,123

(22) Filed: Dec. 27, 2023

(65) Prior Publication Data

US 2024/0215992 A1     Jul. 4, 2024

Related U.S. Application Data

(60) Provisional application No. 63/435,848, filed on Dec. 29, 2022.

(51) Int. Cl.
*A61B 17/34* (2006.01)
*A61B 17/16* (2006.01)

(52) U.S. Cl.
CPC ...... *A61B 17/1635* (2013.01); *A61B 17/3472* (2013.01)

(58) Field of Classification Search
CPC ........... A61B 17/1635; A61B 17/3472; A61B 17/1667; A61B 17/17
See application file for complete search history.

(56) References Cited

U.S. PATENT DOCUMENTS

| | | | | |
|---|---|---|---|---|
| 2,301,500 A | * | 11/1942 | Anderson .......... | A61B 17/1721 606/103 |
| 5,324,295 A | * | 6/1994 | Shapiro .............. | A61B 17/1714 606/86 R |
| 2008/0086142 A1 | * | 4/2008 | Kohm ................ | A61B 17/3472 606/92 |
| 2018/0344330 A1 | * | 12/2018 | Thibodeau ......... | A61B 17/1796 |

* cited by examiner

*Primary Examiner* — Tessa M Matthews
(74) *Attorney, Agent, or Firm* — SCHWEGMAN LUNDBERG & WOESSNER, P.A.

(57)     ABSTRACT

Methods and devices for delivering bone material are disclosed. The bone delivery device may include a cannula and a cartridge in fluid communication with the cannula, wherein the cartridge comprises a base containing one or more delivery channels configured to receive bone material. The bone material within the delivery channel(s) is compacted to a second diameter smaller than the first diameter. The method includes actuating the compacted bone material from the cartridge through the cannula to deliver the bone material to an implantation site.

15 Claims, 24 Drawing Sheets

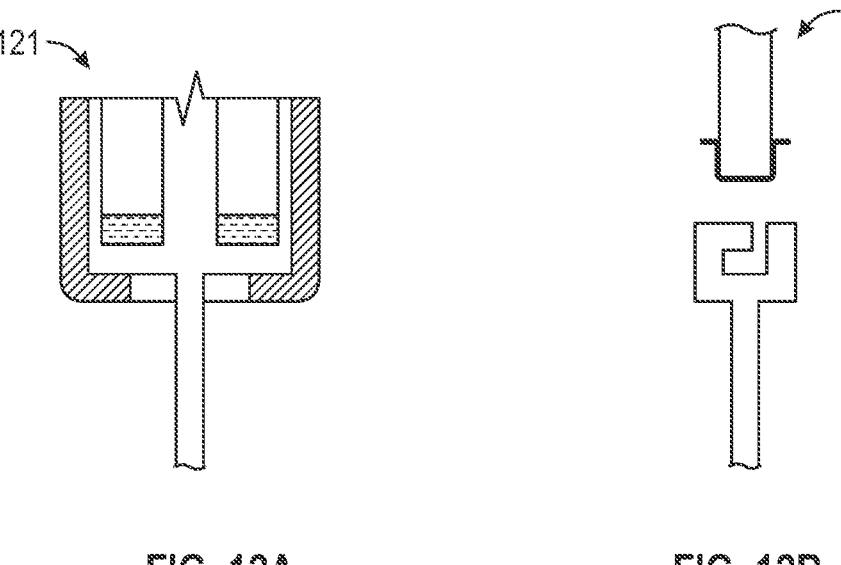
FIG. 12A                    FIG. 12B
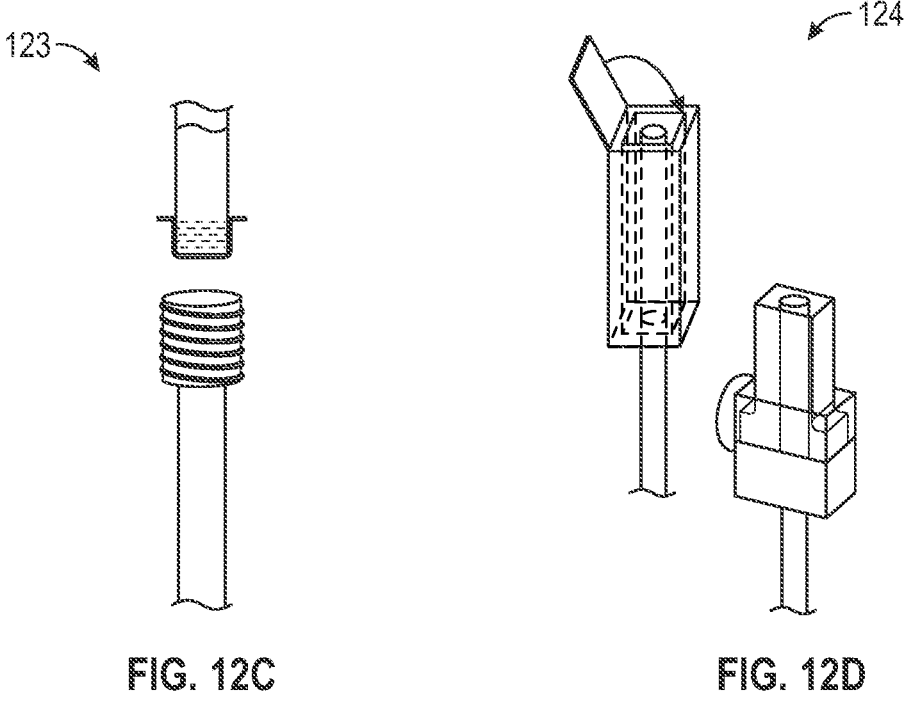
FIG. 12C                    FIG. 12D

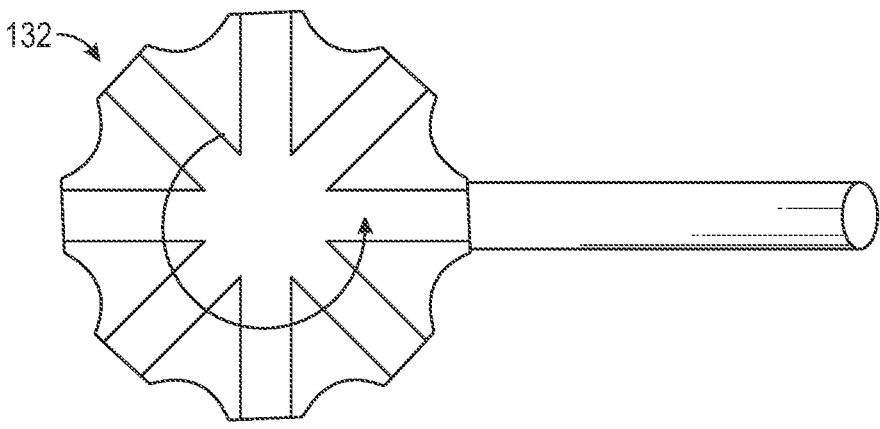
FIG. 13
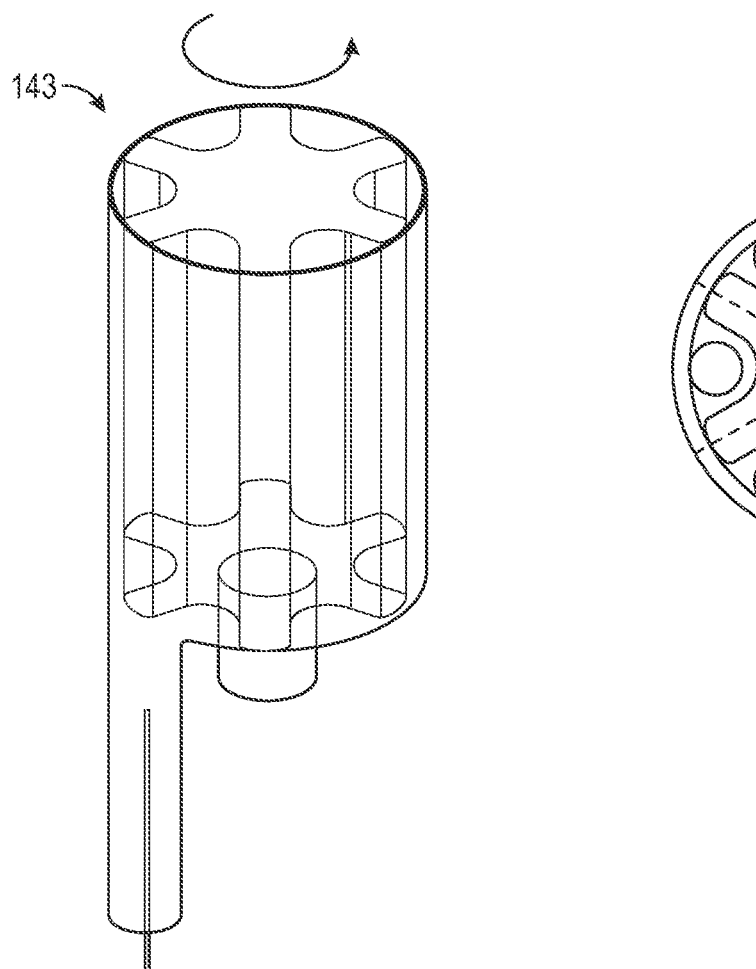
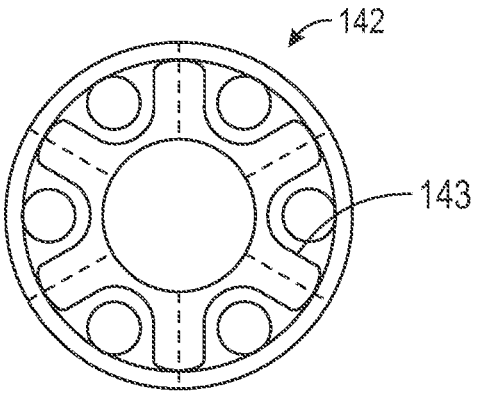
FIG. 14B
FIG. 14A

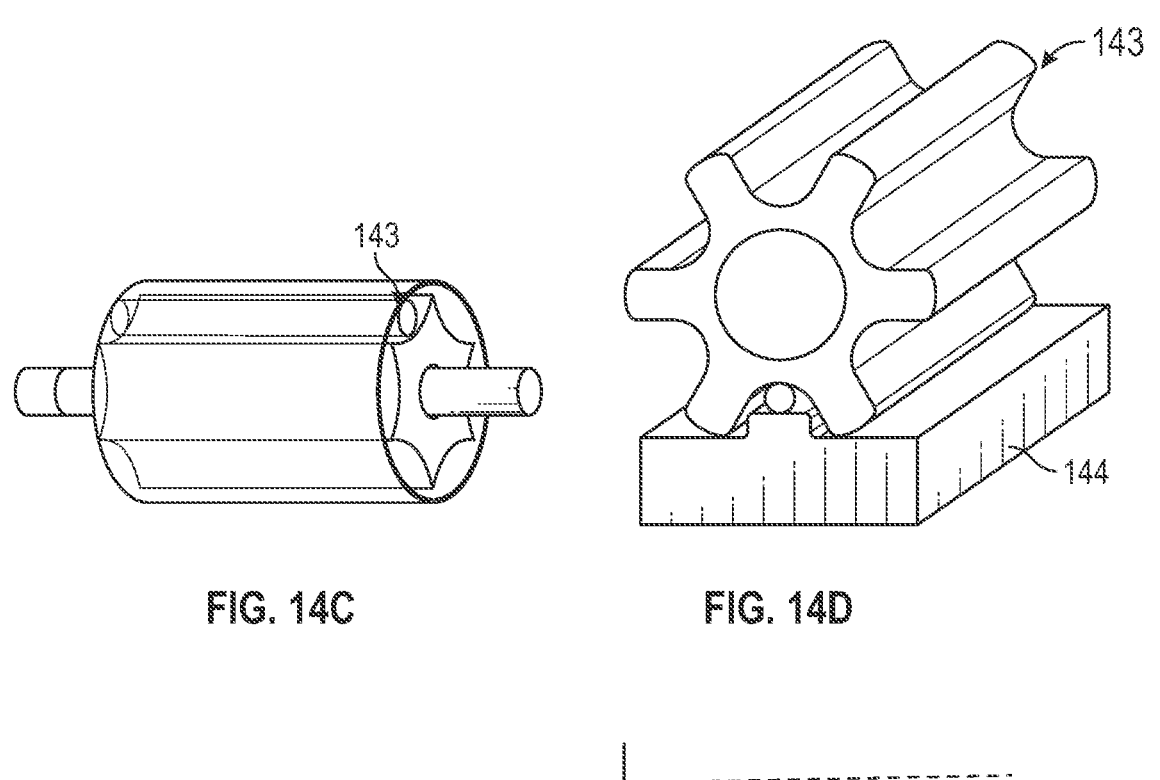
FIG. 14C          FIG. 14D
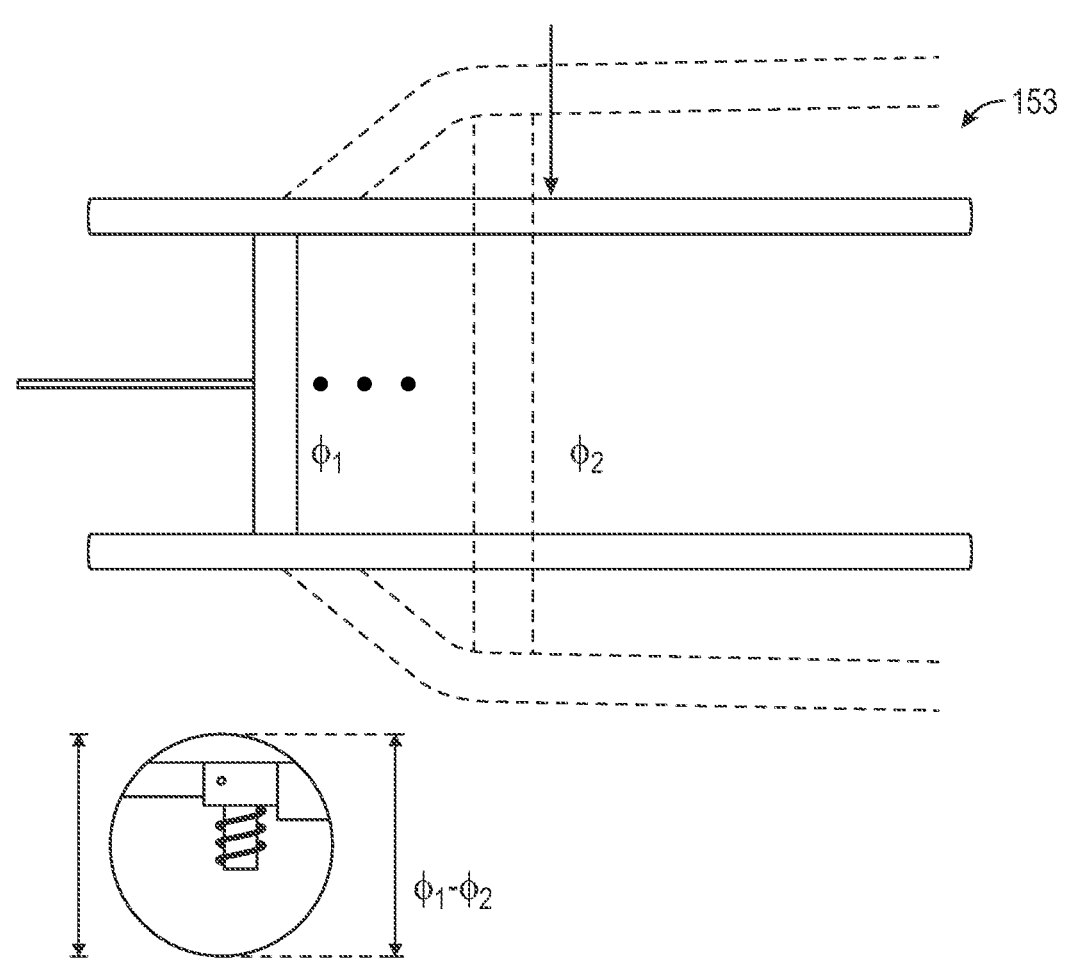
FIG. 15

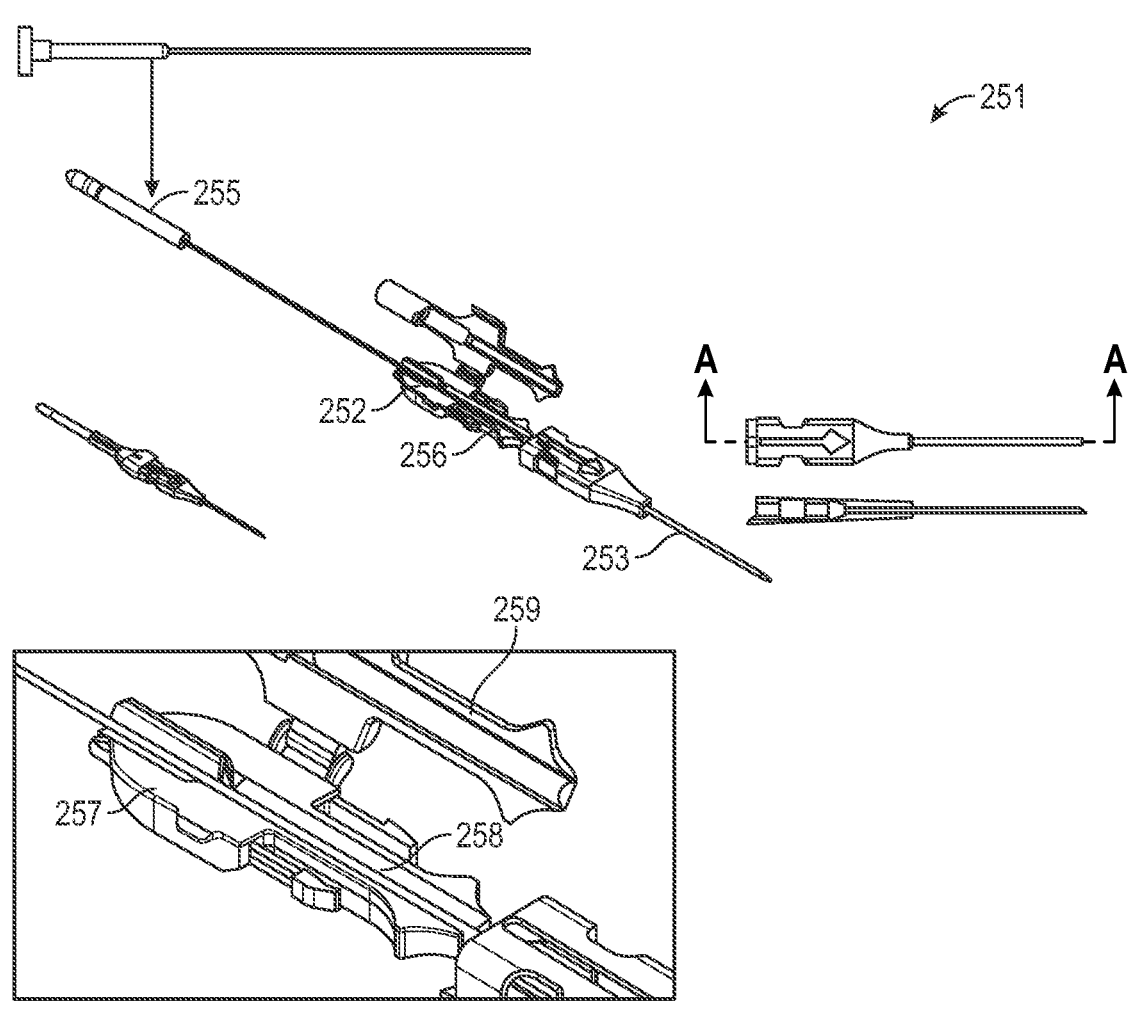
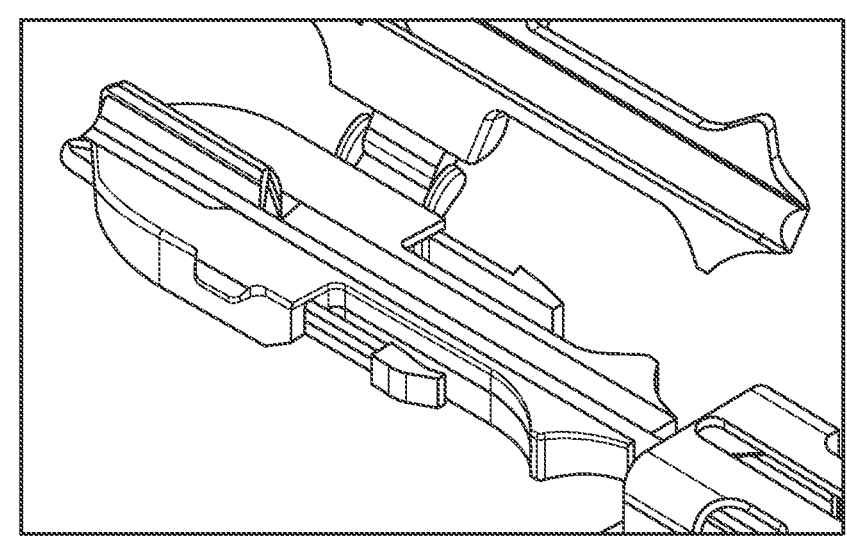
FIG. 25

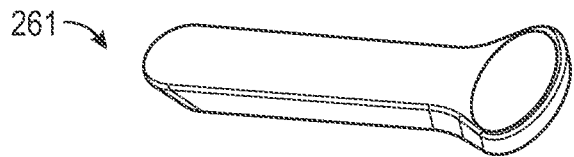
261
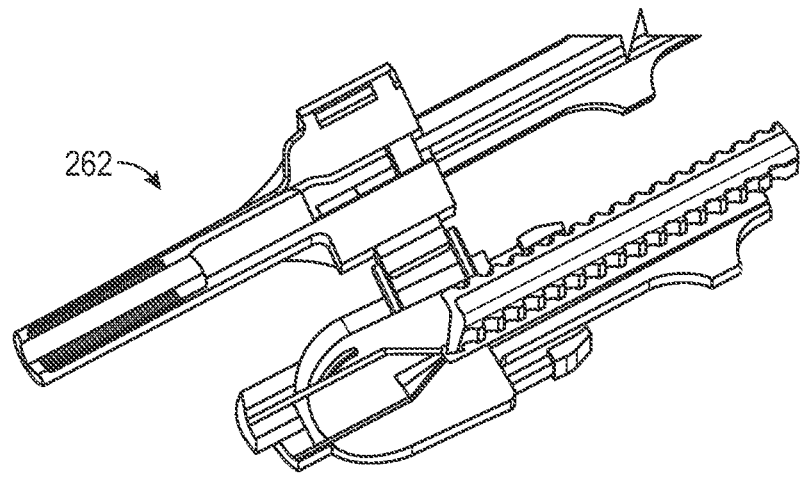
262
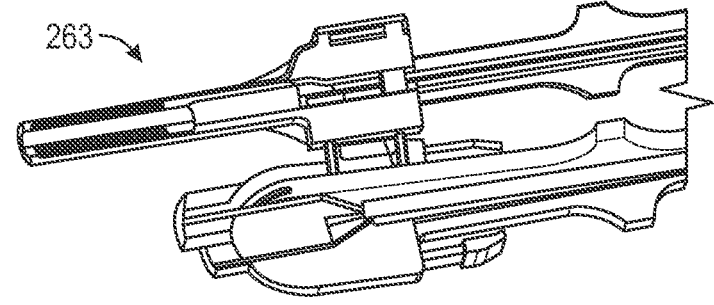
263
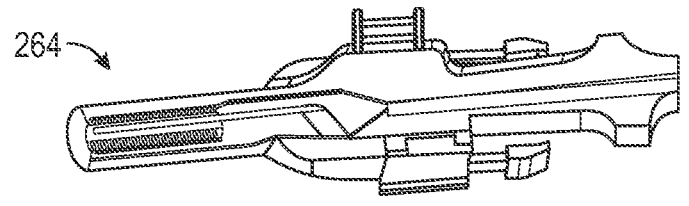
264
FIG. 26A

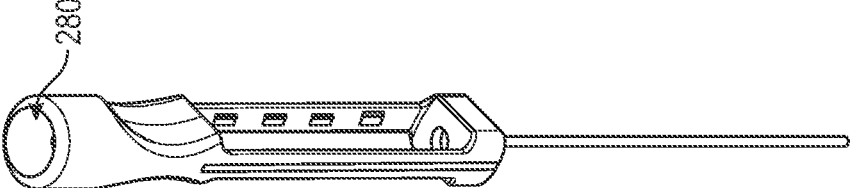
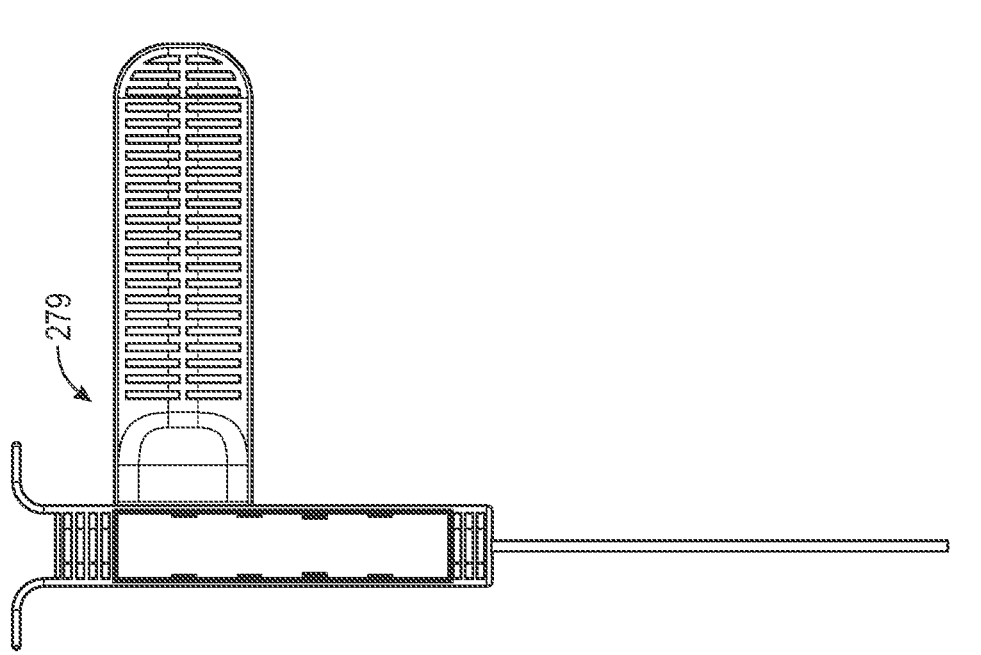
FIG. 27B

BONE GRAFT DELIVERY DEVICES AND METHOD

CLAIM OF PRIORITY

This application claims the benefit of U.S. Provisional Patent Application Ser. No. 63/435,848, filed on Dec. 29, 2022, the benefit of priority of which is claimed hereby, and which is incorporated by reference herein in its entirety.

SUMMARY/TECHNICAL FIELD

Methods and devices for delivering bone graft material are disclosed.

BACKGROUND

Bone grafts are used in various orthopaedic surgical procedures, including surgical procedures that require the fusion, healing, or joining of boney defects or deficits. There are orthopaedic needs to deploy bone graft into a confined space through a minimally invasive approach with the utilization of a delivery cannula. Currently, the delivery of autologous bone or allogenic bone graft may cause clogging in the delivery cannulas utilized in the operating room.

BRIEF DESCRIPTION OF THE DRAWINGS

FIGS. 12A-D schematically show mechanisms for connection of a single delivery channel cartridge to a delivery cannula according to the present disclosure.

FIG. 13 schematically shows a cartridge rotatably connectable to a bone delivery cannula.

FIGS. 14A-D schematically shows views of an alternative embodiment of a cartridge incorporating a graft cartridge with delivery channels circumferentially arranged according to the present disclosure.

FIG. 15 schematically shows a cross-section view of an expandable delivery cannula.

FIG. 25 schematically shows a perspective view of a bone delivery device including a cartridge having a single delivery channel and a hinged lid according to the present disclosure.

FIGS. 26A and 26B schematically show a method of loading bone material into the bone delivery device of FIG. 25.

FIGS. 27A and 27B schematically show variations of hand grips located on a bone delivery device.

DETAILED DESCRIPTION

Figure 1:
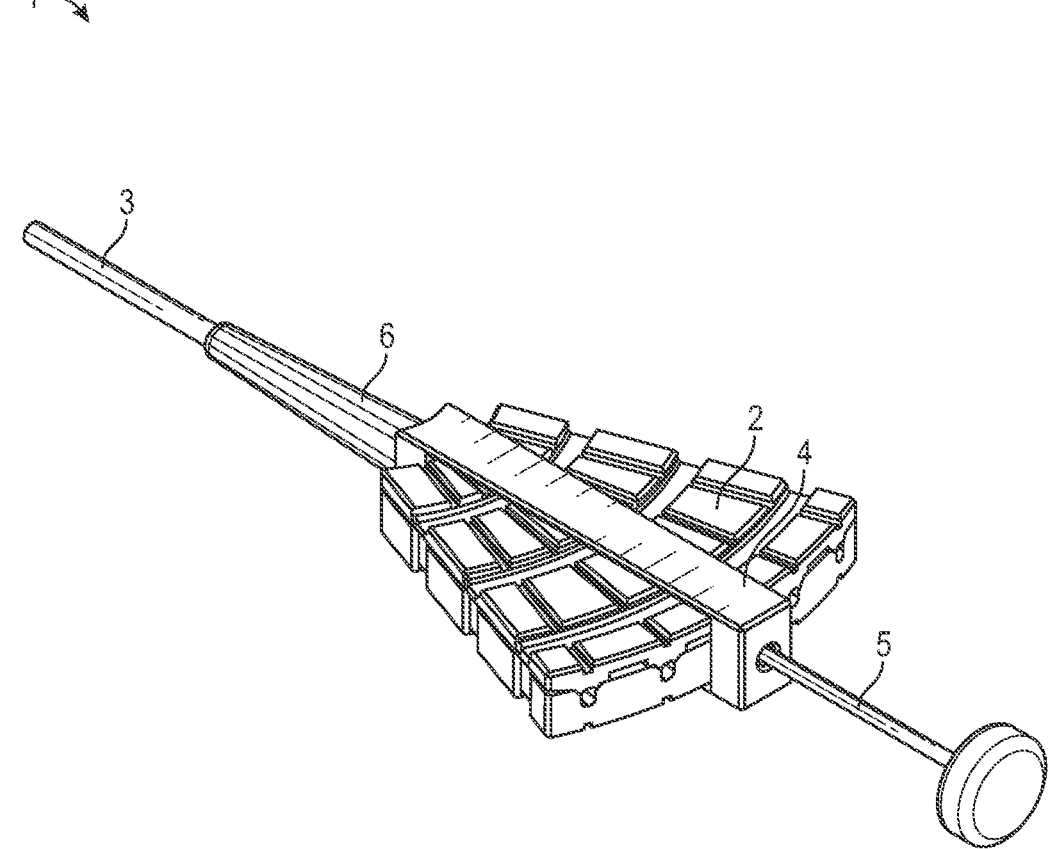
FIG. 1 schematically shows a perspective view of a bone delivery device including a cartridge having multiple graft delivery channels arranged linearly according to the present disclosure.
Figure 3:
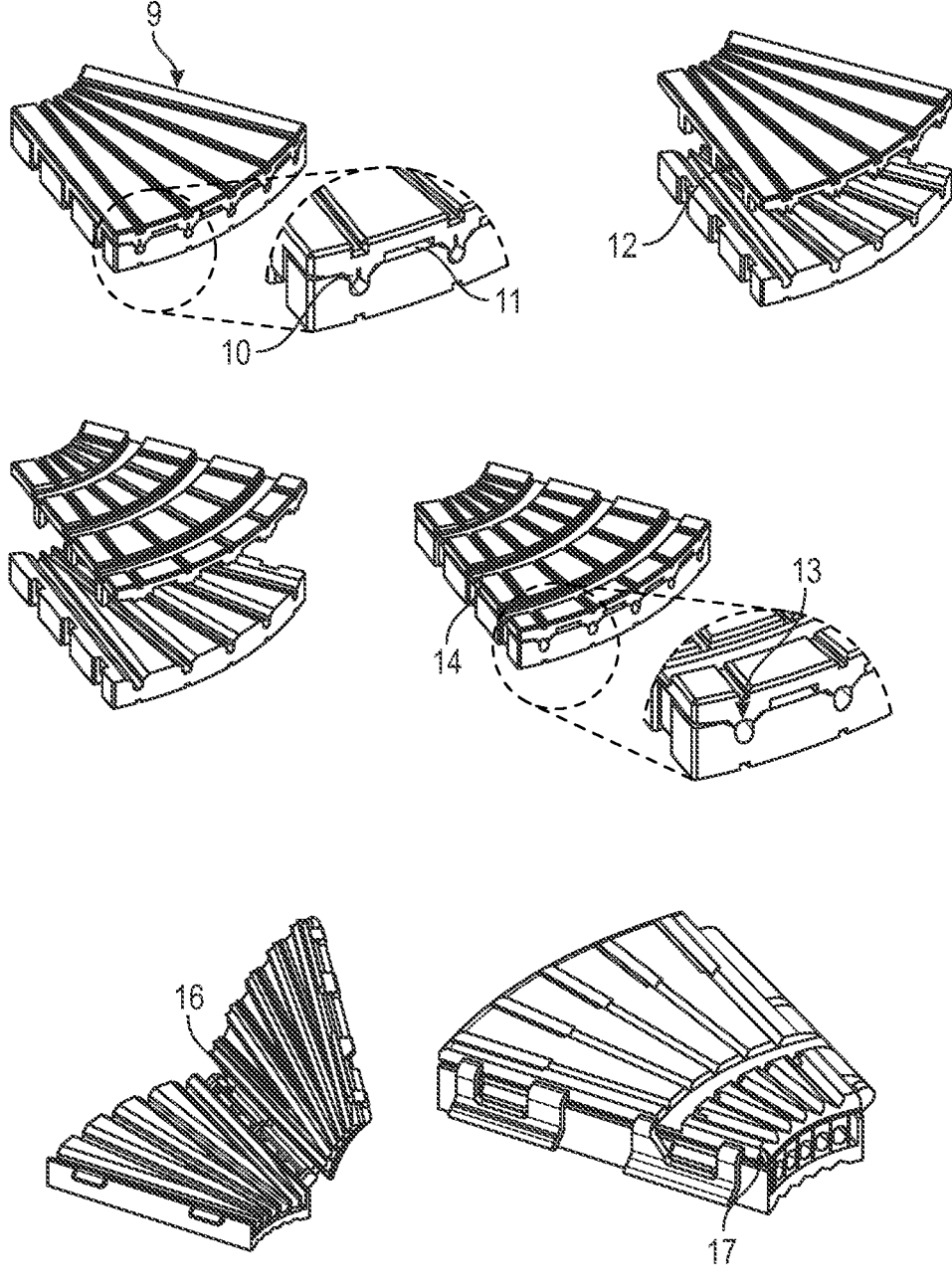
FIG. 3 schematically shows a compacting mechanism of the cartridge of FIG. 1.

FIG. 1 schematically shows a perspective view of a multi-channel bone delivery device 1 including a cartridge 2. The cartridge 2 can contain a single or multiple graft delivery channels and is in fluid communication with a proximal end of a delivery cannula 3 to deliver bone material through a distal end of the cannula 3. In some embodiments, the cartridge 2 is composed of a transparent material to provide visual feedback of bone material advancement. In other embodiments, the cartridge 2 is composed of solid/opaque material. The bone delivery device may be used to deliver bone material which is harvested from a patient (autologous graft) that is also the intended recipient of the bone material. Alternatively, the bone delivery device may be used for the delivery of allogenic or bone synthetic substitutes. Alternatively, the bone delivery device may be used for the delivery of autologous graft, allogenic or synthetic substitutes, or a combination therein. In some embodiments, the cartridge 2 includes physical guide features configured to enable insertion of the cartridge 2 into the device 1 in only one direction and/or orientation. The cartridge 2 is connectable to the frame 4 of the device 1, as explained in more detail with reference to FIG. 3. The device 1 may further include a grip feature 6 providing a tactile surface for a user to grasp the device 1.

The cannula 3 may be structured to support delivery of bone material for orthoscopic/arthroscopic procedures and/or for minimally invasive surgical procedures. The diameter of the cannula 3 may be 1 mm, 2 mm, 3 mm, 4 mm, 5 mm, 6 mm, 7 mm, 8 mm, 9 mm, 10 mm, 11 mm, 12 mm or any diameter there between or lesser/greater thereof. In some embodiments, the diameter of the cannula 3 is less than 6 mm. At such sizes, delivery of bone material, particularly of cancellous bone material, is difficult using conventional devices/systems because the bone material tends to clog the cannula. The combination of the cartridges and cannulas of the bone delivery devices discussed herein address the difficulty of delivering bone material in smaller, more precise, delivery mechanisms. The combination of graft moving from a smaller diameter to a larger diameter further addresses the challenge of bone graft delivery. In this embodiment, the graft delivery channel diameter is smaller than the diameter of the cannula.

The device 1 further includes a plunger 5 configured to actuate bone material out of the cartridge 2 and through the cannula 3 to a delivery site. In some embodiments, the plunger 5 may include a rubber end configured to push the bone marrow (that is 'juiced out' of the bone material as the bone material is compacted and advanced) in the direction of travel of the bone material. This marrow would act as a lubricant to keep the bone material advancing. In some embodiments, plunger 5 can be configured to rotate while moving axially. The rotational movement of the plunger rotates the bone material, keeping the material from binding up in any one rough/mismatched area of the cartridge 2 and delivery cannula 3. The plunger rod distal end may be designed with 'fingers' configured to grab onto the bone material to rotate the bone material.

Figure 2:
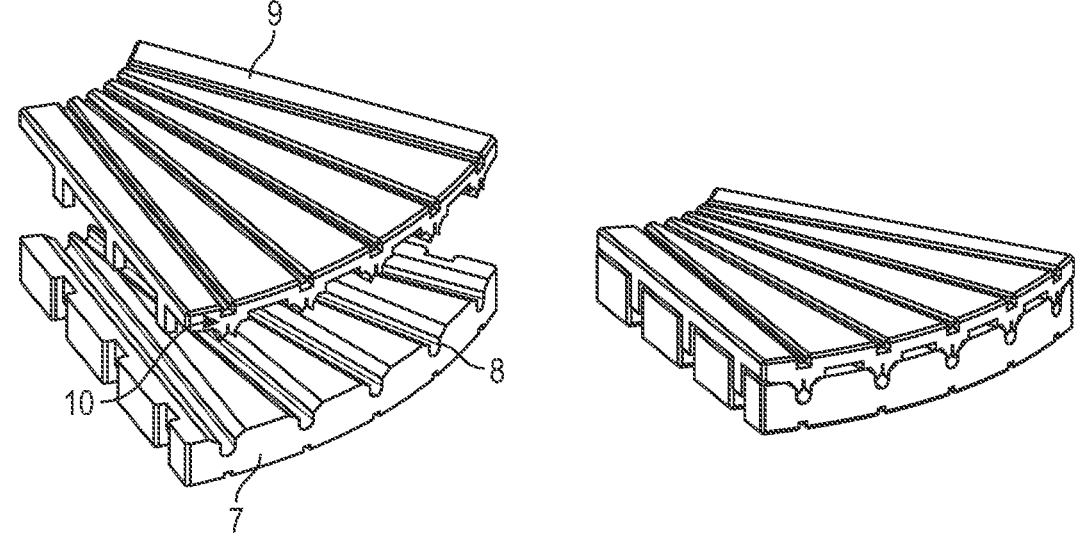
FIG. 2 schematically shows the cartridge of FIG. 1 in an open position and a closed position.

FIG. 2 schematically shows the cartridge 2 of FIG. 1 in an open position and a closed position. The cartridge 2 may include a base 7 including one or more delivery channels 8 configured for housing bone material for implantation. Each delivery channel 8 may be composed of a non-porous smooth surface of suitable polymer or metal. The cartridge 2 may further include a loading lid 9 including one or more protrusions 10 configured to compact the bone material within the one or more delivery channels 8. In an open position, base 7 is not joined to lid 9. In a closed position base 7 is joined to lid 9. The channels can have a chamfered opening or otherwise include one or more chamfered edges to facilitate easier loading of the bone, for example, where a longitudinal edge of the channel that engages or otherwise cooperates with a protrusion of the loading lid is chamfered.

FIG. 3A schematically shows the compacting mechanism of the cartridge 2 of FIG. 1. First, bone material is loaded into one or more delivery channels 8 within base 7. Then the loading lid 9 is joined to the base 7. The loading lid 9 includes one or more protrusions 10 that are configured to compact the bone material to a diameter that is a smaller diameter than the cannula 3. The loading lid 9 may include one or more gaps 11 connected to the one or more protrusions 10 to capture the flow of excess bone material from the one or more delivery channels 8. An alternate embodiment of this cartridge can include a hinge design or other assembly interface 16 as depicted in FIG. 3B. In this embodiment, a user can compress the bone graft into the graft delivery channel and then close lid. The lid maintains a clearance between the top of the compressed bone and lid 17. Clips can be implemented to secure the closure of the graft cartridge.

After bone compaction, a user may expand the one or more delivery channels 8 to a diameter that provides clearance to the compacted bone. In some embodiments, the delivery channels 8 are expanded by about 1 millimeter in diameter. The expansion can be accomplished by replacing the loading lid 9 with a delivery lid 12, or by changing the positioning of the loading lid on the base. The delivery lid 12 may include one or more protrusions 13 sized to provide a delivery channel 8 diameter substantially matching the diameter of the cannula 3. In some embodiments, the delivery lid 12 is configured to snap lock to the base 7. In some embodiments, the delivery lid 12 further includes one or more tracks 14 configured to attach the assembled cartridge 2 to the frame 4. The expansion can also be accomplished by lifting the loading lid 9 by approximately 1 millimeter, for example, where a movable loading lid can occupy a first position relative to the base corresponding to a first delivery channel diameter for compacting bone material and then can be moved to a second position relative to the base corresponding to a second delivery channel diameter that is larger than the first diameter. In this regard, in some embodiments, a single lid can provide loading, compacting and delivering capabilities.

Figure 4:
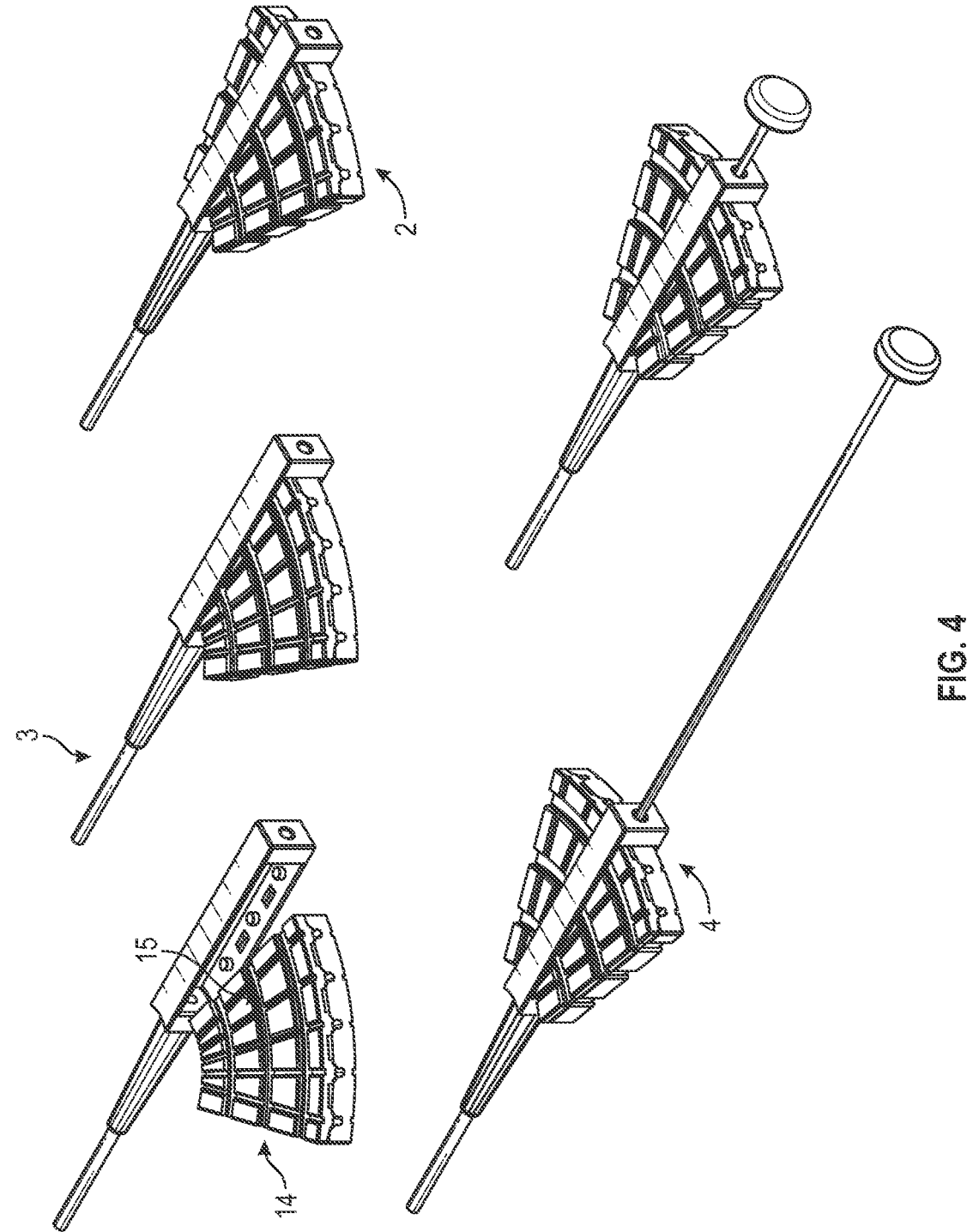
FIG. 4 schematically shows joining the cartridge to the bone delivery cannula of FIG. 1.

FIG. 4 schematically shows joining the cartridge 2 to the bone delivery device 1 of FIG. 1. As depicted in FIG. 4, cartridge 2 may include a configuration of tracks 14 and notches 15 as the communicative features between the cartridge 2 and frame 4. Alternatively, the cartridge 2 may be connected to the frame 4 by magnetic communication, pin notch orientation, gear teeth, or other suitable connection means between the cartridge 2 and frame 4. The cartridge 2 communicates with the frame 4 in a manner such that the cartridge 2 can be advanced such that each delivery channel 8 aligns concentrically with the delivery cannula 3. In some embodiments, the user receives tactile feedback when a delivery channel 8 containing bone material is aligned with the cannula 3 to determine distinct loading positions. In other embodiments, a user receives auditory feedback indicating when subsequent graft delivery channels are aligned with the delivery cannula. After delivery of graft from all channels, the user is able to disconnect the graft cartridge and connect another cartridge to continue bone graft delivery.

Figure 5:
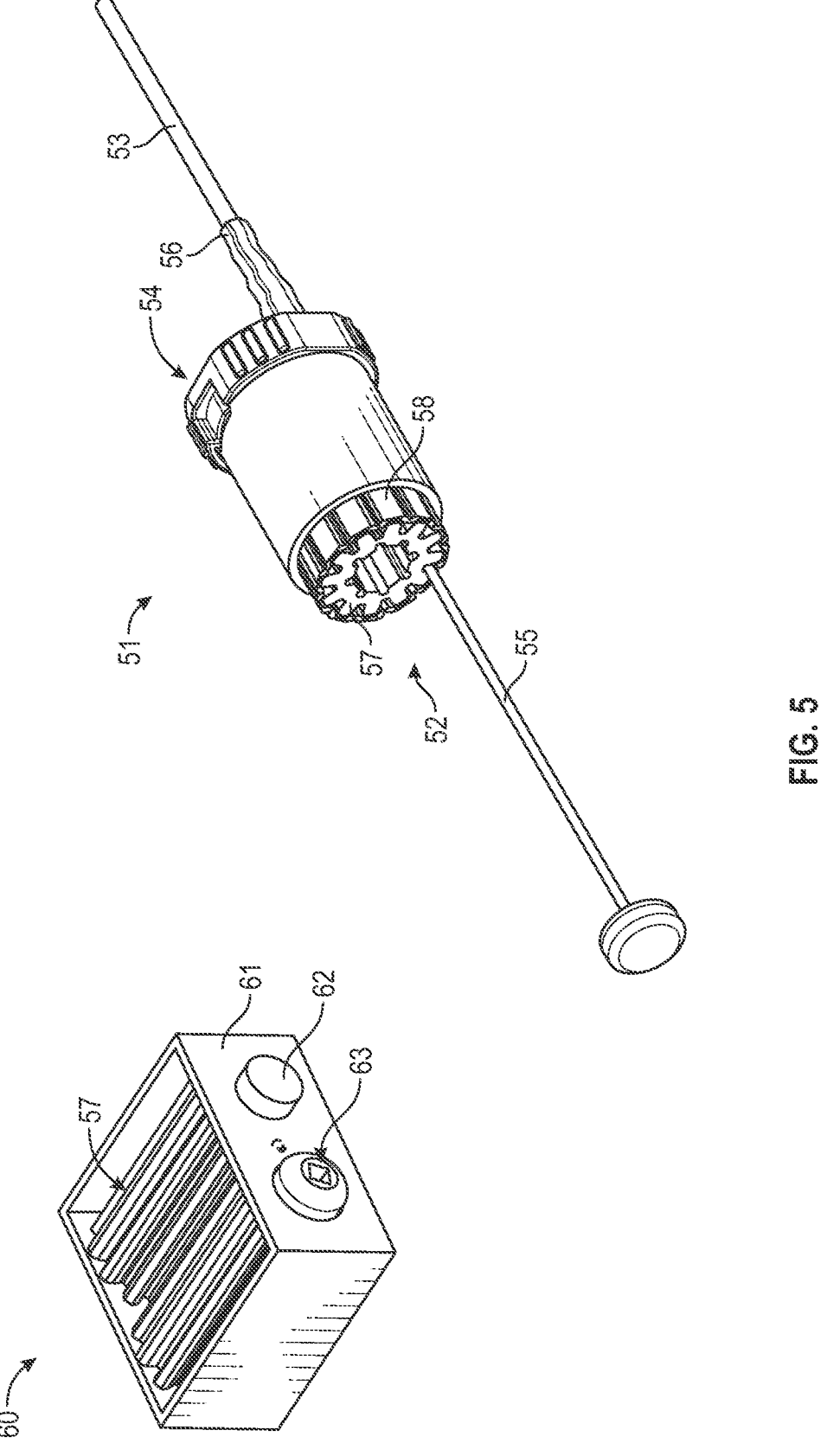
FIG. 5 schematically shows views of a bone delivery device including a cartridge incorporating a circumferential arrangement of delivery channels according to the present disclosure.

FIG. 5 schematically shows views of a bone delivery device 51 including a cartridge 52 incorporating an elongated gear shape 57 that contains a plurality of bone graft channels orientated circumferentially. The gear 57 may be inserted into a sleeve 58 to contain loaded bone graft. Sleeve 58 maintains a clearance between sleeve and compressed bone graft within the channel to aid delivery. Bone delivery device 51 further includes a frame 54 configured to receive the geared cartridge 52 and sleeve 58 to communicate a delivery path with cannula 53. When loaded within the frame 54, bone material housed within the gear 57 and sleeve 58 is in fluid communication with the cannula 53. In some embodiments, bone delivery device 51 further includes a grip feature 56 and/or a plunger rod 55. In some embodiments, gear 57 and sleeve 58 can be transparent for visualization of the delivery of the bone material.

The gaps between the teeth of gear 57 may constitute delivery channels configured to house bone material for delivery through the cannula 53. To load the gear 57 with bone material, the bone material may be added to a configuration of two gears 57 within a loading assembly 60. The loading assembly 60 may include a housing 61, two axles 62, and one or more torque knobs 63. Each gear 57 may be situated around an axle 62. The loading assembly 60 compacts bone material into the channels of the loading cartridge 52 when rotating the gears 57 about each other.

Figure 6:
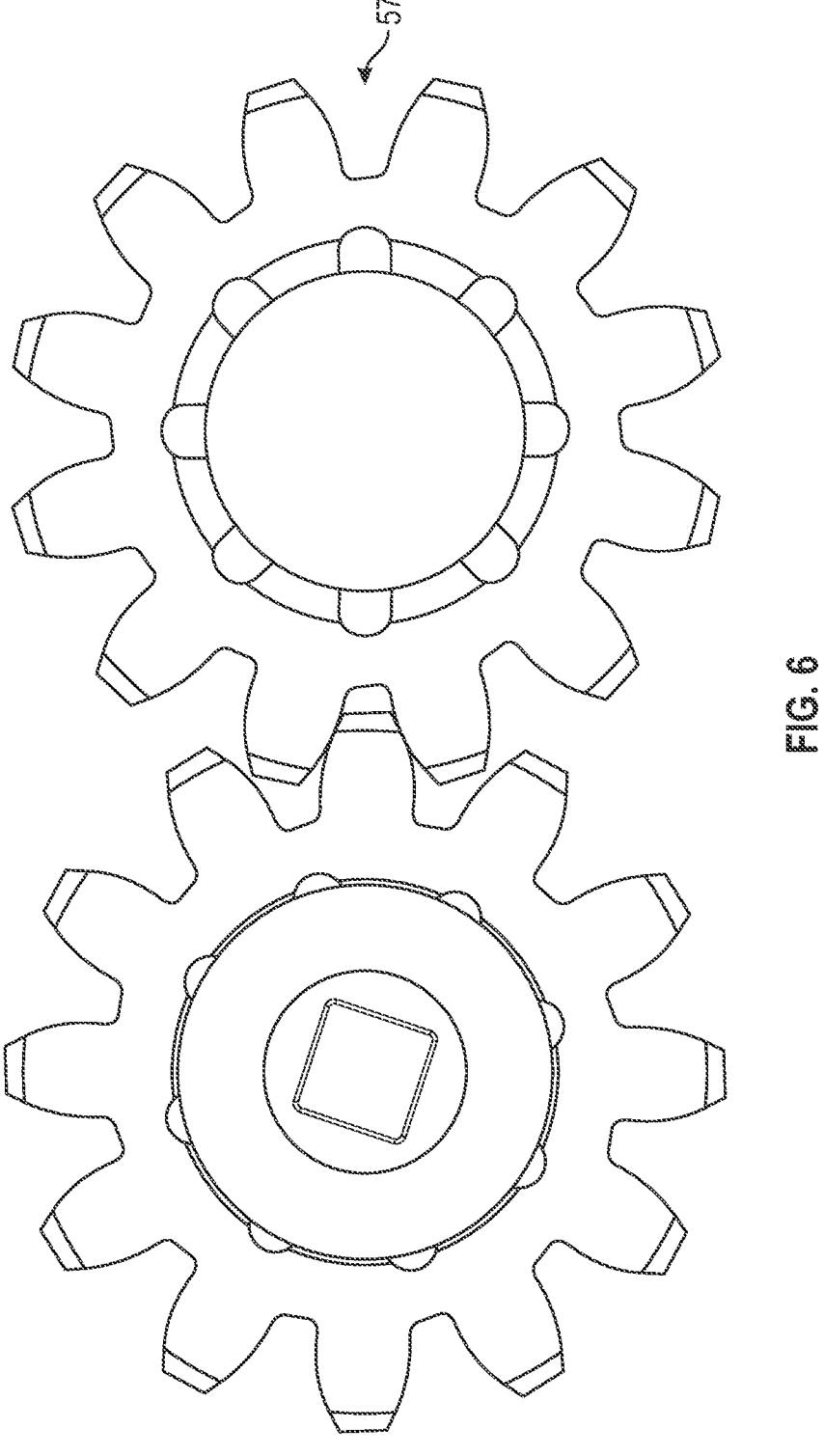
FIG. 6 schematically shows gears for compressing bone material.

FIG. 6 schematically shows gears 57 for compressing bone material. Bone material is added to the gaps between teeth of one or more of the gears 57, for example by sprinkling the bone material into the gaps. A user may turn one or more torque knobs 63 to turn one or more of the axles 62, rotating one or more of the gears 57. As the gears 57 rotate, a tooth of one gear 57 interlocks between two teeth of the other gear 57, compressing the bone material situated in a gap between the two teeth.

In an alternative embodiment, bone material situated within a gap between two teeth of a gear 57 may be compressed without the loading assembly 60. For example, a lid component with protrusions may be connected to the gear 57 such that the protrusions are aligned between the teeth of the gear 57, compressing the bone material.

As another alternative, bone material compression may also be performed via manual insertion of bone material and compressing the gap between two teeth manually via a rod or other packing tool that inserts into the gap to press the bone material into the gap prior to loading the gear 57 into the delivery device 51.

Figure 7:
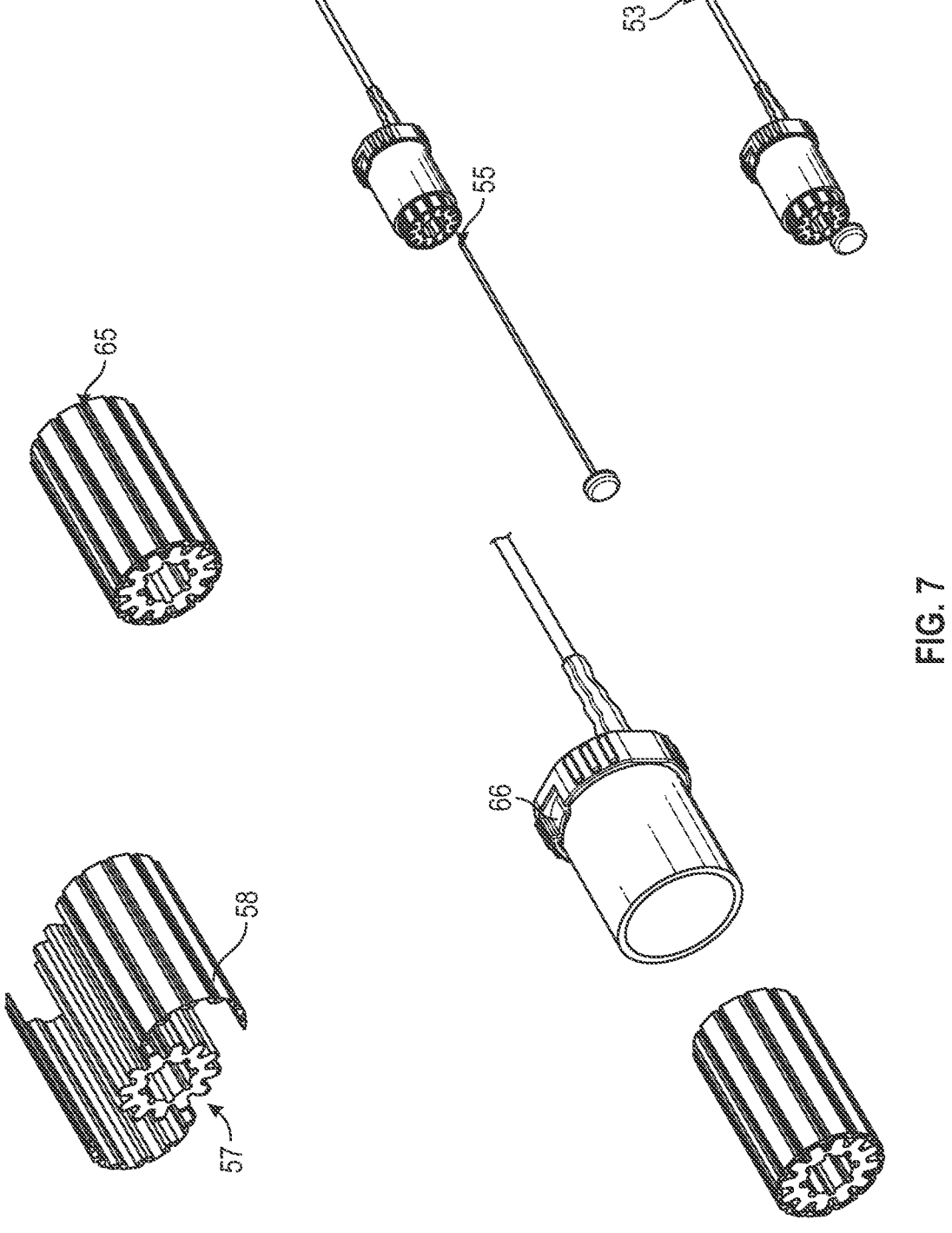
FIG. 7 schematically shows loading of the cartridge of FIG. 5 to a bone delivery device.

FIG. 7 schematically shows loading of the cartridge 52 of FIG. 5. After compression of the bone material, the sleeve 58 may be added to the gear 57. In some embodiments, the sleeve 58 may include two half circle portions that snap into place on the gear 57. In some embodiments, the sleeve 58 may include one or more notches 65 situated on the outer surface of the sleeve 58. The notches 65 are configured to align the sleeve 58 within the frame 54 such that a gap containing bone material is aligned with the delivery cannula 53. In some embodiments, the notches 65 interface with one or more lock tabs 66 situated on the frame 54 to align the bone material. After alignment, a user engages the plunger rod 55 to push the bone material through the delivery cannula 53. After delivery of the bone material, the plunger rod 55 may be retracted and then the user may rotate the sleeved gear cartridge 57 to align the next delivery channel concentrically with the delivery cannula 53.

Figure 8:
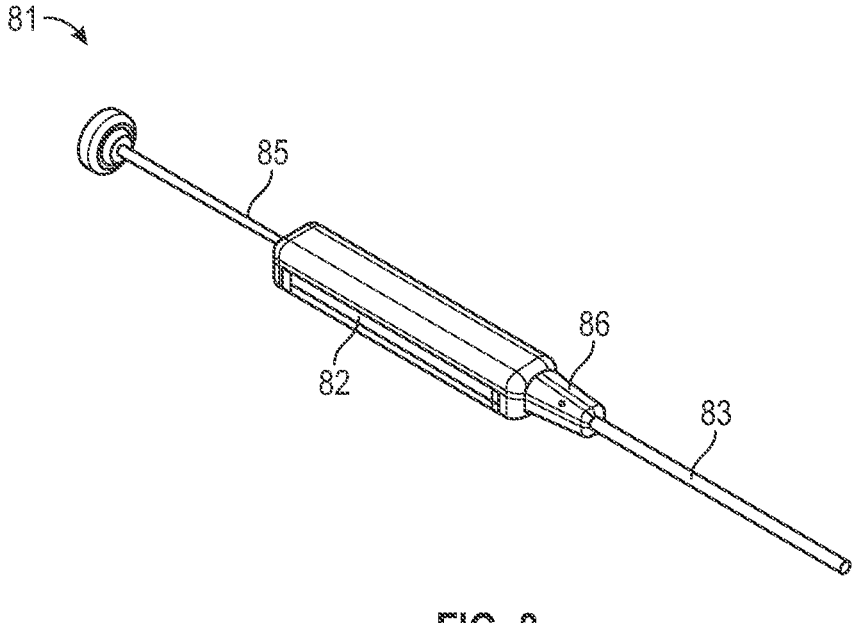
FIG. 8 schematically shows a perspective view of a bone delivery device including a cartridge having a single delivery channel according to the present disclosure.

FIG. 8 schematically shows a perspective view of a bone delivery device 81 including a cartridge 82 having a single delivery channel 88. Bone delivery device 81 may include a cannula 83, plunger 85, and grip feature 86 similar to cannula 3, plunger 5, and grip feature 6 of bone delivery device 1. In some embodiments, after actuation of bone material within the cartridge 82 by the plunger 85, the plunger 85 may be withdrawn and the cartridge 82 may be replaced with a new, preloaded single delivery channel cartridge.

Figure 9A:
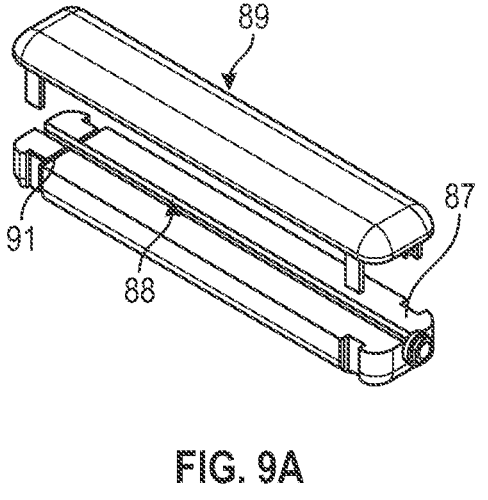
FIG. 9A schematically shows compression lid of the cartridge of FIG. 8. to compress bone into delivery channel.
Figure 9B:
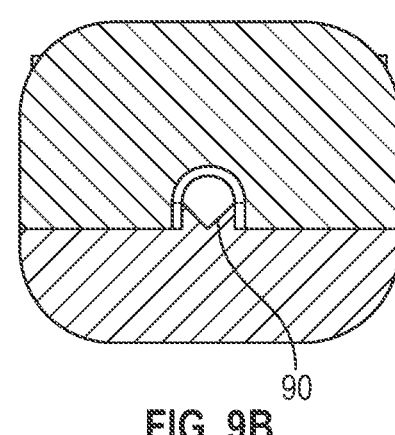
FIG. 9B shows a cross section of the compression lid and cartridge of FIG. 9A.

FIG. 9A schematically shows loading of the cartridge 82 of FIG. 8. The cartridge 82 may include a base 87 including one delivery channel 88 configured for housing bone material for implantation. The delivery channel 88 may be composed of a non-porous smooth surface of suitable polymer or metal. In some embodiments, the base 87 further includes an indicator 91 adjacent to the delivery channel 88 to illustrate a desired fill line for a user filling the delivery channel 88 with bone material. Additional demarcation to guide a user can be placed to inform a user of graft fill location. The cartridge 82 may further include a loading lid 89 including one or more protrusions 90 configured to compact the bone material within the delivery channel 88. The loading lid compresses the bone graft to create clearance between the compacted bone and the delivery lid. A packing tool can also be utilized instead of a loading lid in this embodiment to compress the bone graft. In some embodiments, the cartridge 82 further includes threading 92 situated on an end of the cartridge 82 configured to join to the grip feature 86 and/or cannula 83. The threading 92 may include partial or interrupted threads. The threading 92 may be situated on a stem situated on a distal end of the cartridge 82 and the cannula 83 may include mated threads. Threading can be a clipped design or other mechanical communication for connecting and disconnecting the delivery cannula from the graft cartridge.

Figure 10:
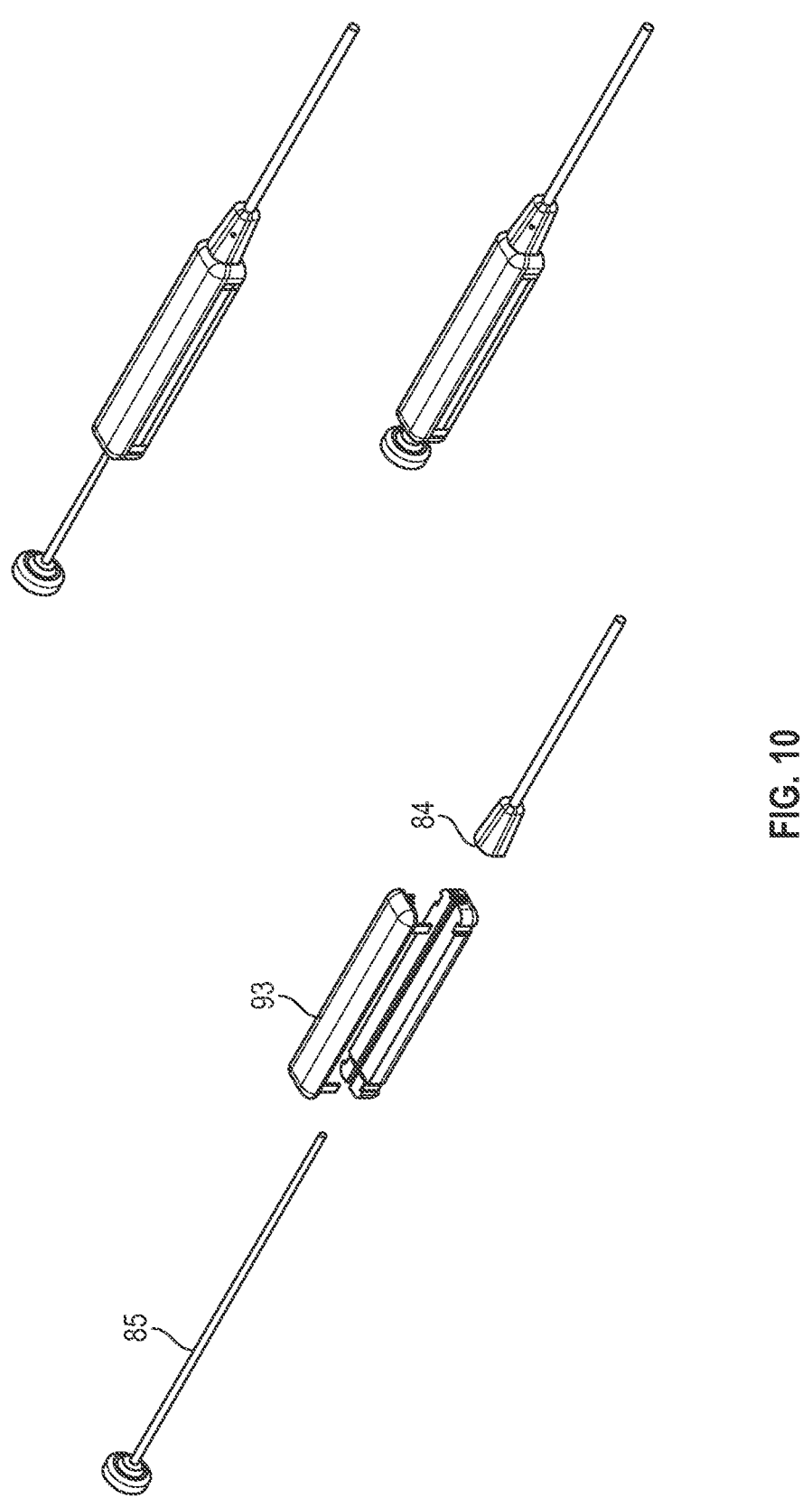
FIG. 10 schematically shows joining the cartridge to the bone delivery cannula of FIG. 8.

FIG. 10 schematically shows joining the cartridge 82 to the bone delivery device 81 of FIG. 8. The bone material may be loaded into the delivery channel 88. Then the loading compaction lid 89 is joined to the base 87. The loading compaction lid 89 includes one or more protrusions 90 that are configured to compact the bone material to a diameter that is smaller than the diameter of the cannula 83. The loading compaction lid 89 is then replaced with a delivery lid 93. Lid 93 maintains a clearance between the compressed bone graft and the delivery lid. Delivery lid 93 and base 87 are then attached to the cannula 83, for example by mating the threading 92 to the cannula 83. Before or after attaching the cartridge 82 to the cannula 83, the plunger 85 may be partially inserted into the cartridge 82 without displacing the bone material. The plunger 85 may then be actuated to progress the bone material through a distal end of the cannula 83 and into an implantation site.

After delivering the bone material, the plunger 85 may be withdrawn from the cannula 83 and cartridge 82. Then the depleted cartridge may be removed from cannula 83 and then replaced with a new cartridge containing bone material.

Figure 11A:
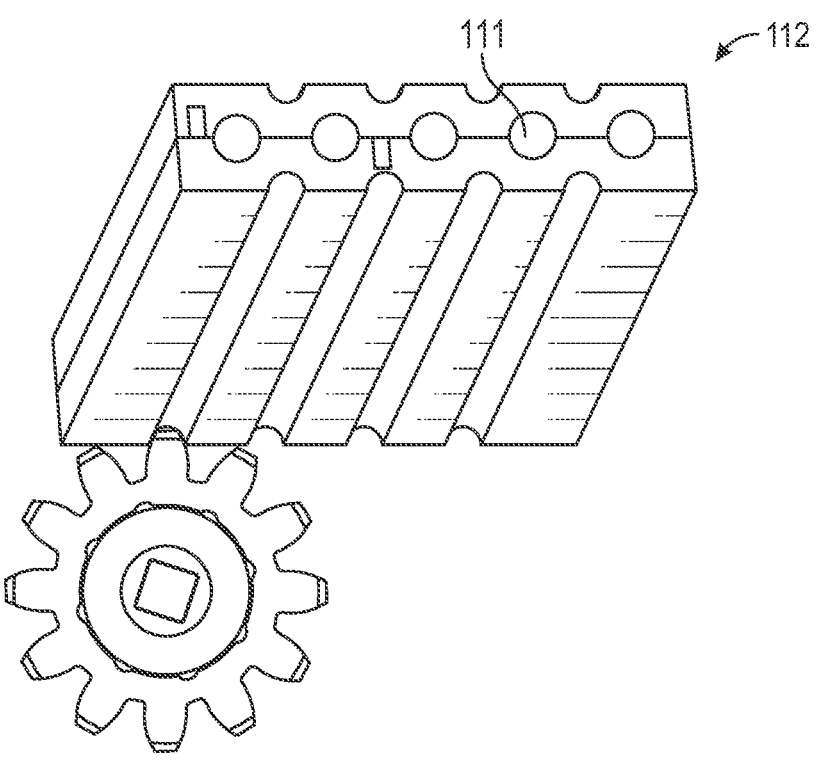
FIGS. 11A and 11B schematically show a cartridge slidably connectable to a bone delivery device according to the present disclosure.
Figure 11B:
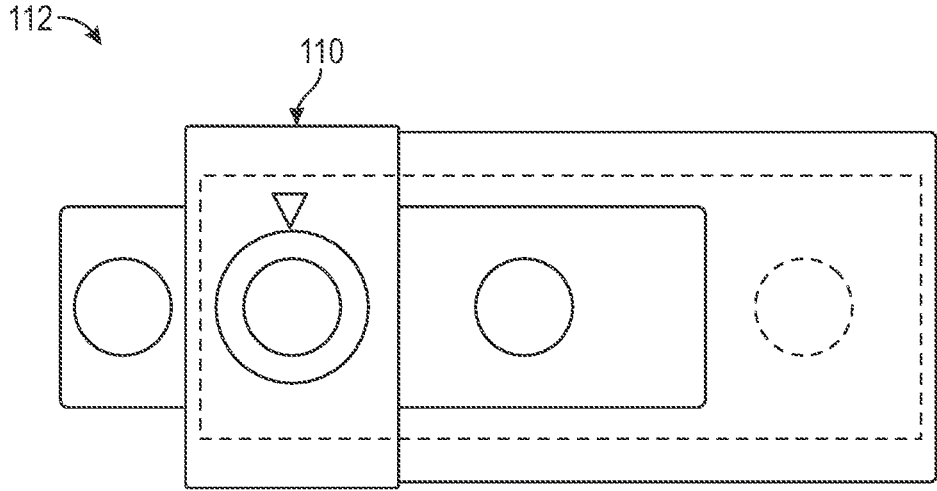

FIGS. 11A and 11B schematically show a cartridge 112 slidably connectable to a bone delivery device 110. In some embodiments, a user may slide the cartridge 112 through a frame of the device 110 to align a delivery channel 111 containing bone material with a plunger and cannula. After actuating the plunger to push the bone material in a delivery channel through the delivery cannula, the user may withdraw the plunger, and slide the cartridge 112 to align a subsequent delivery channel containing bone material with the cannula for follow on bone graft delivery.

FIGS. 12A-D schematically show mechanisms for connection of a single delivery channel cartridge to a delivery cannula. For smaller bone volumes a single delivery channel that can be easily attached and removed from a delivery cannula may be desirable. Attachment mechanisms may include, but are not limited to, magnets 121, a bayonet lock 122, a threaded connection 123, a snap lock 124, or a hinge lock (not shown).

FIG. 13 schematically shows a cartridge 132 rotatably connectable to a bone delivery device. The cartridge 132 may be a disc that rotates to align the bone material loaded delivery channels with the delivery cannula.

FIGS. 14A-D schematically shows views of an alternative embodiment of a cartridge 142 incorporating an elongated gear 143. In some embodiments, cartridge 142 incorporates rack and pinion compression wherein bone material is loaded in a gap between two teeth of the gear 143 and then the gear 143 is rolled onto a rack 144 to further compress the bone material into the delivery channel.

FIG. 15 schematically shows a cross-section view of an expandable delivery cannula 153. In some embodiments, the plunger of a bone delivery device is composed of expandable material and delivery cannula 153 is either rendered expandable via slits along the length of the cannula 153 or the cannula 153 is composed of elastic material. Cannula 153 may be composed of hydrophobic material to further reduce friction during of delivery of bone material through a cannula.

Figure 16:
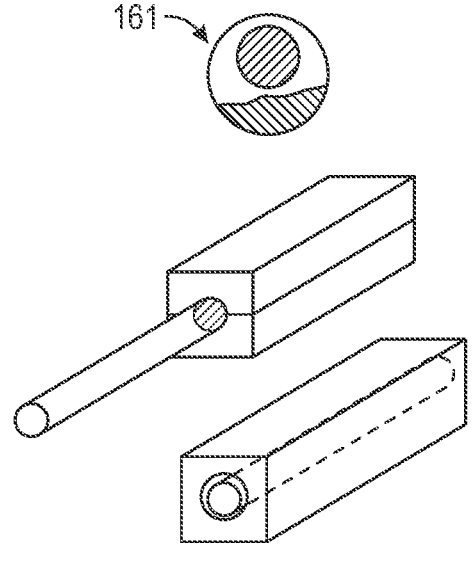
FIG. 16 schematically shows a cartridge delivery channel including a removable spacer.

FIG. 16 schematically shows a cartridge delivery channel including a spacer 161. In some embodiments, a spacer 161 may be placed in a delivery channel during loading of bone material. After compression of the bone material, the spacer 161 is pulled out of the delivery channel to create space between the bone material and delivery channel. The created space reduces friction during of delivery of bone material.

Figure 17:
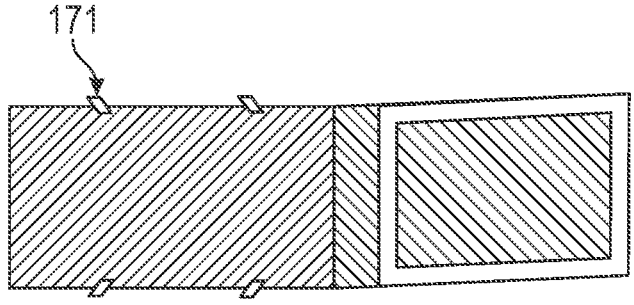
FIG. 17 schematically shows a delivery cannula including overflow vent holes for excess material.

FIG. 17 schematically shows a delivery cannula including clearance holes 171. In some embodiments, clearance holes 171 may be situated along the length of a delivery cannula. The clearance holes 171 may be configured to allow bone material to eject from the cannula during advancement, reducing friction during delivery of the bone material. Clearance holes can also provide venting to the delivery cannula to reduce the pressure of delivery. This can be achieved with one or more through holes in the delivery cannula. The delivery cannula can be composed of micropores to allow "outgassing" or pressure relief by decreasing surface area of contact between delivery cannula and an accumulated amount of bone graft.

Figure 18:
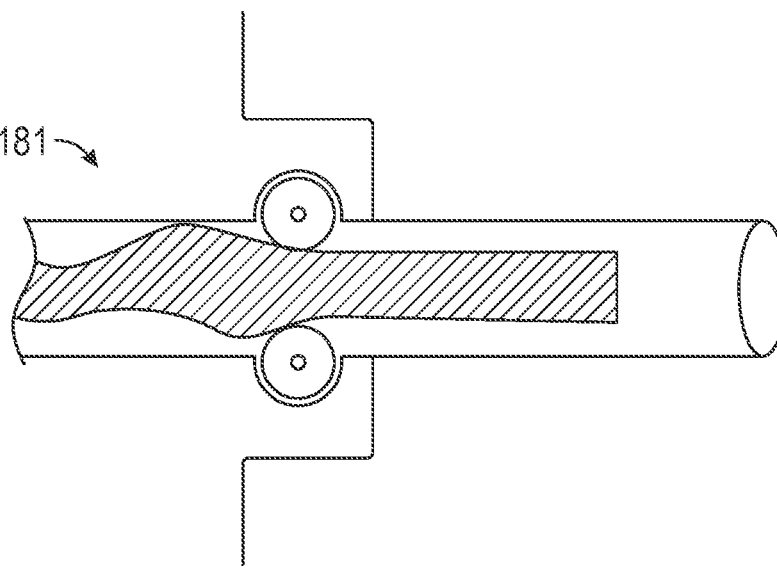
FIG. 18 schematically shows a delivery cannula including graft compression rollers.

FIG. 18 schematically shows a delivery cannula including rollers 181. In some embodiments, one or more rollers 181 may be situated at the connection of the frame and cannula. The rollers 181 may be configured to compress the diameter of the bone material as the material advances out of a cartridge and into the cannula. In some embodiments, after the bone material passes through the rollers 181 there is clearance between the bone material and the delivery cannula, reducing friction during of delivery of the bone material. The rollers 181 may be configured as a single roller or a double roller. Rollers also compress the bone graft material into a molded linear structure preventing the bone graft from radial expansion during the delivery.

Figure 19:
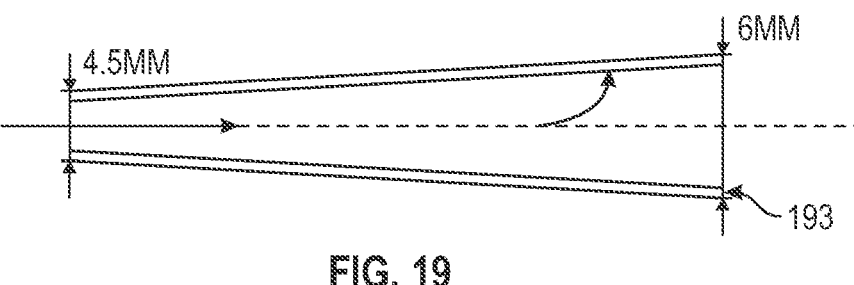
FIG. 19 schematically shows a tapered delivery cannula or delivery channel.

FIG. 19 schematically shows a tapered delivery cannula 193. In some embodiments, cannula 193 may include an outward taper from a proximal end to a distal end of the cannula 193, providing progressively more clearance between the compressed bone material and the delivery cannula 193 as the bone material is actuated towards the distal end of the cannula 193, reducing friction during of delivery of the bone material. A taper may also be applied to any of the aforementioned delivery channels themselves, aiding in the transfer of compressed bone material from the delivery channel into the delivery cannula.

Figure 20:
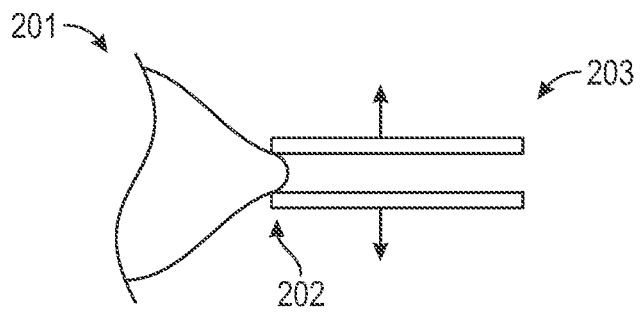
FIG. 20 schematically shows a delivery cannula connected to a funnel with a stepped neck.

FIG. 20 schematically shows a delivery cannula 203 connected to a funnel 201 with a stepped neck 202. In some embodiments, bone material may be forced/pushed through the small diameter of the neck 202 before entering the larger diameter of the delivery cannula 203. Delivery cannula 203 may be made of an elastic or expandable material to further facilitate ease of delivery. In some embodiments, delivery cannula 203 could be made 'flexible' by cutting one or more slits down the length of the cannula.

Figure 21:
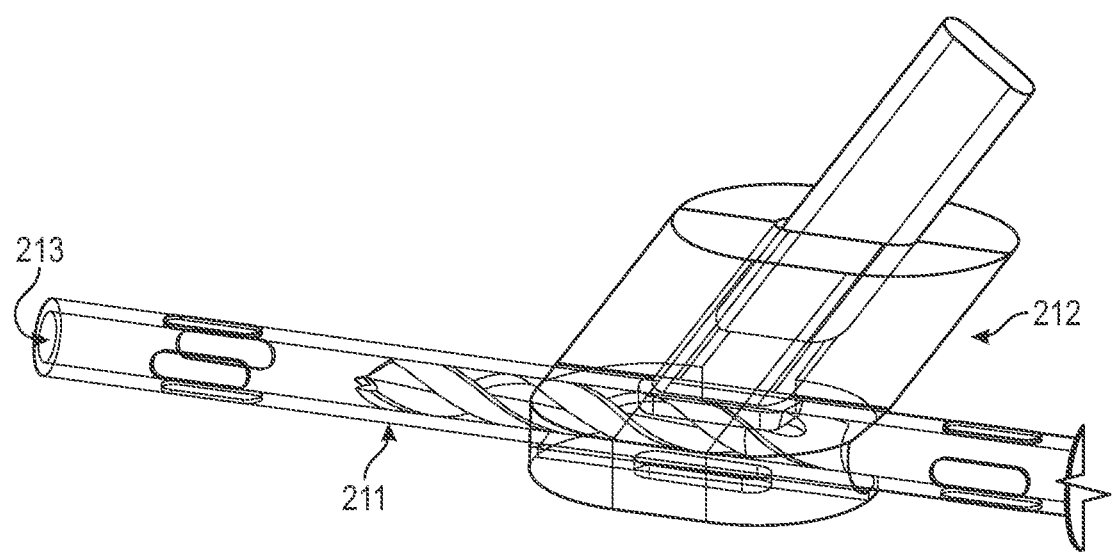
FIG. 21 schematically shows bone material loaded through a hopper into a delivery cannula connected to an auger.

FIG. 21 schematically shows bone material loaded through a hopper 212 into a delivery cannula 213 connected to an auger 211. In some embodiments, a bone delivery device may include a plunger system configured such that a user may actuate an auger 211 to move bone material continuously as the bone material is fed into the system. Bone material may be fed through the hopper 212 and pressed down with a plunger into a rotating auger bit of the auger 211 to advance the bone material along the length of the delivery cannula 213.

Figure 22:
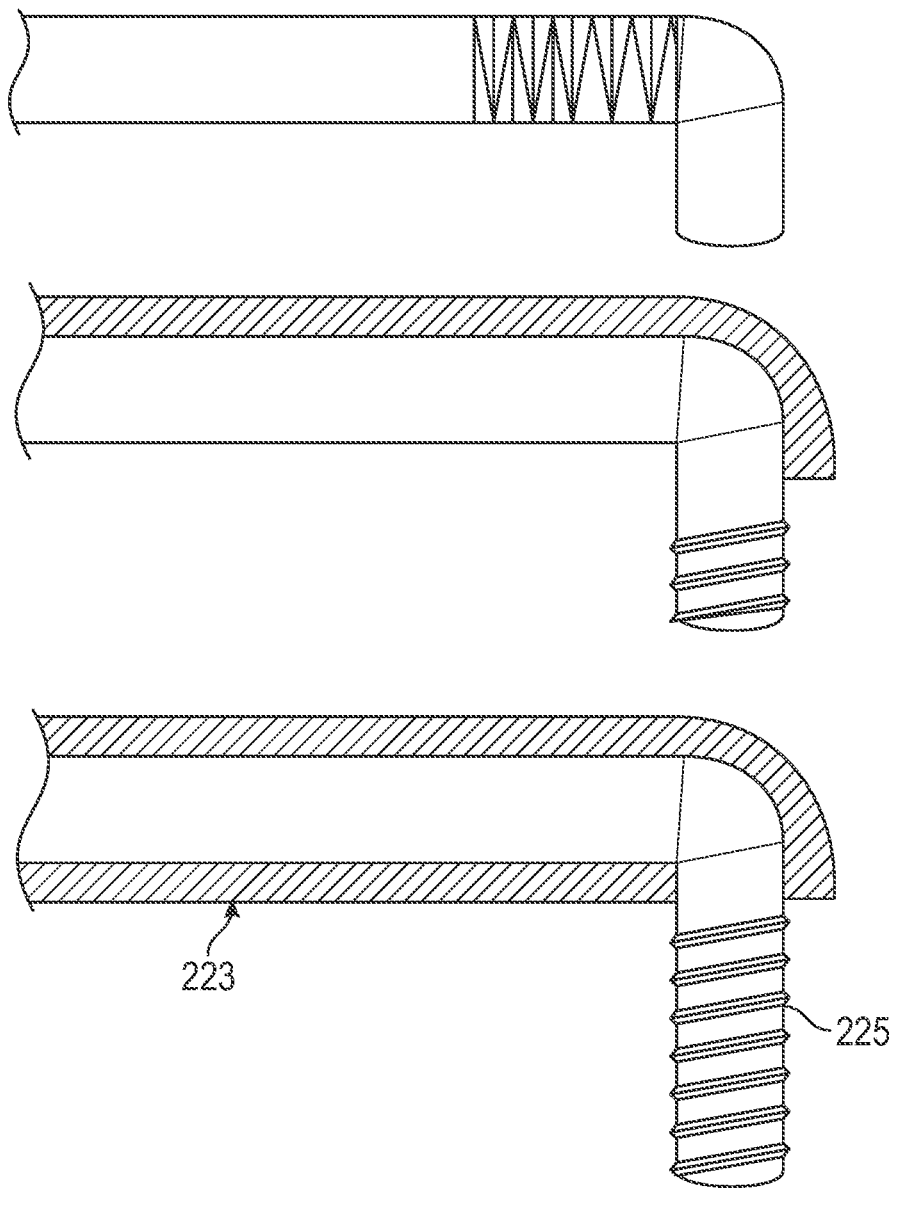
FIG. 22 schematically shows a flexible plunger in use with a delivery cannula.

FIG. 22 schematically shows a flexible plunger 225 in use with a delivery cannula 223. In some embodiments, plunger 225 may be flexible or include a bendable section. Plunger 225 may be configured to, after plunging bone material out of the cannula 223, continue past the distal opening of cannula 223 and serve as a 'tamp' to pack the delivered bone material into a delivery site, for example a cyst. In some embodiments, a user may pack a delivery site with a straight cannula of a bone delivery device for axial packing of bone material after each delivery.

Figure 23:
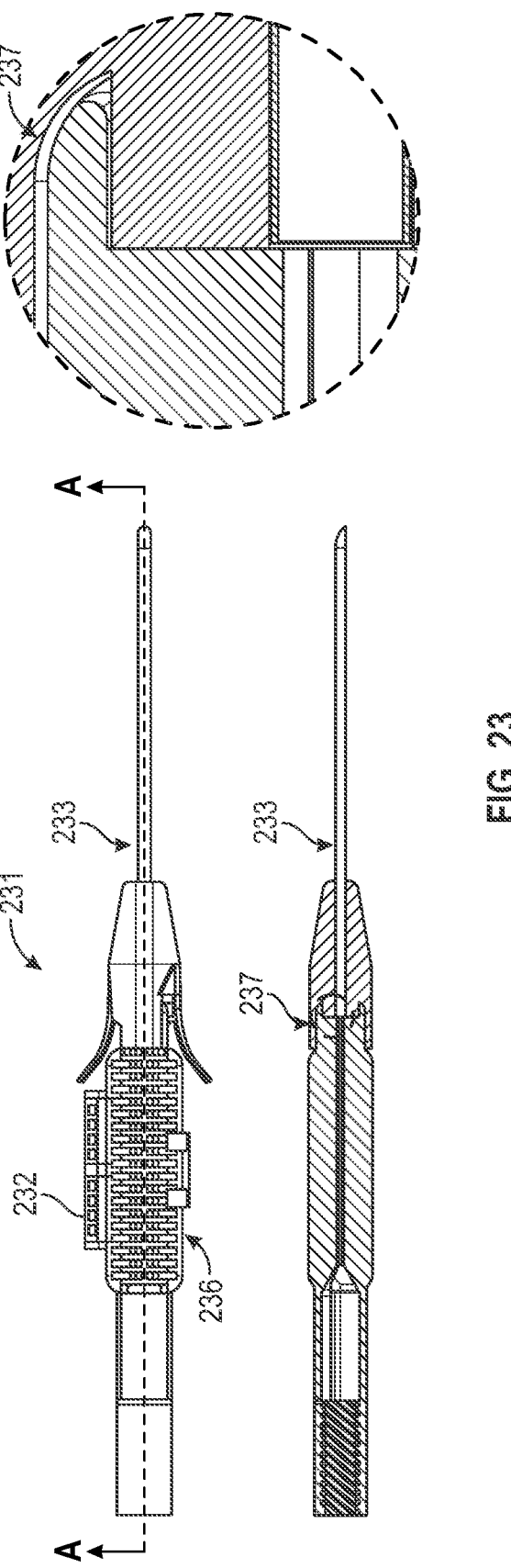
FIG. 23 schematically shows a dual clip feature employed in a bone delivery device.

FIG. 23 schematically shows a dual clip feature employed in a bone delivery device 231. Bone delivery device 231 includes a cannula 233 and grip feature 236 similar to cannula 83, plunger 85, and grip feature 86 of bone delivery device 81. Cannula 233 may include a sheath with a transparent window to allow a user to visually identify bone material situated within the cannula 233. The bone delivery device 231 includes two winged clips 237 employed to connect the cartridge 232 to the delivery cannula 233. One clip 237 is situated on each of the opposing sides of the cartridge 232. Engagement of the cartridge 232 and cannula 233 with the dual clips 237 decreases the chance of a user unintentionally disconnecting the cartridge 232 and cannula 233 during use. In some embodiments, the clips 237 may be colored to enable a user to better identify the clips 237 when connecting the clips 237 to the cannula 233. The cannula 233, or a portion thereof, may be colored with a different color than the clips 237.

Figure 24:
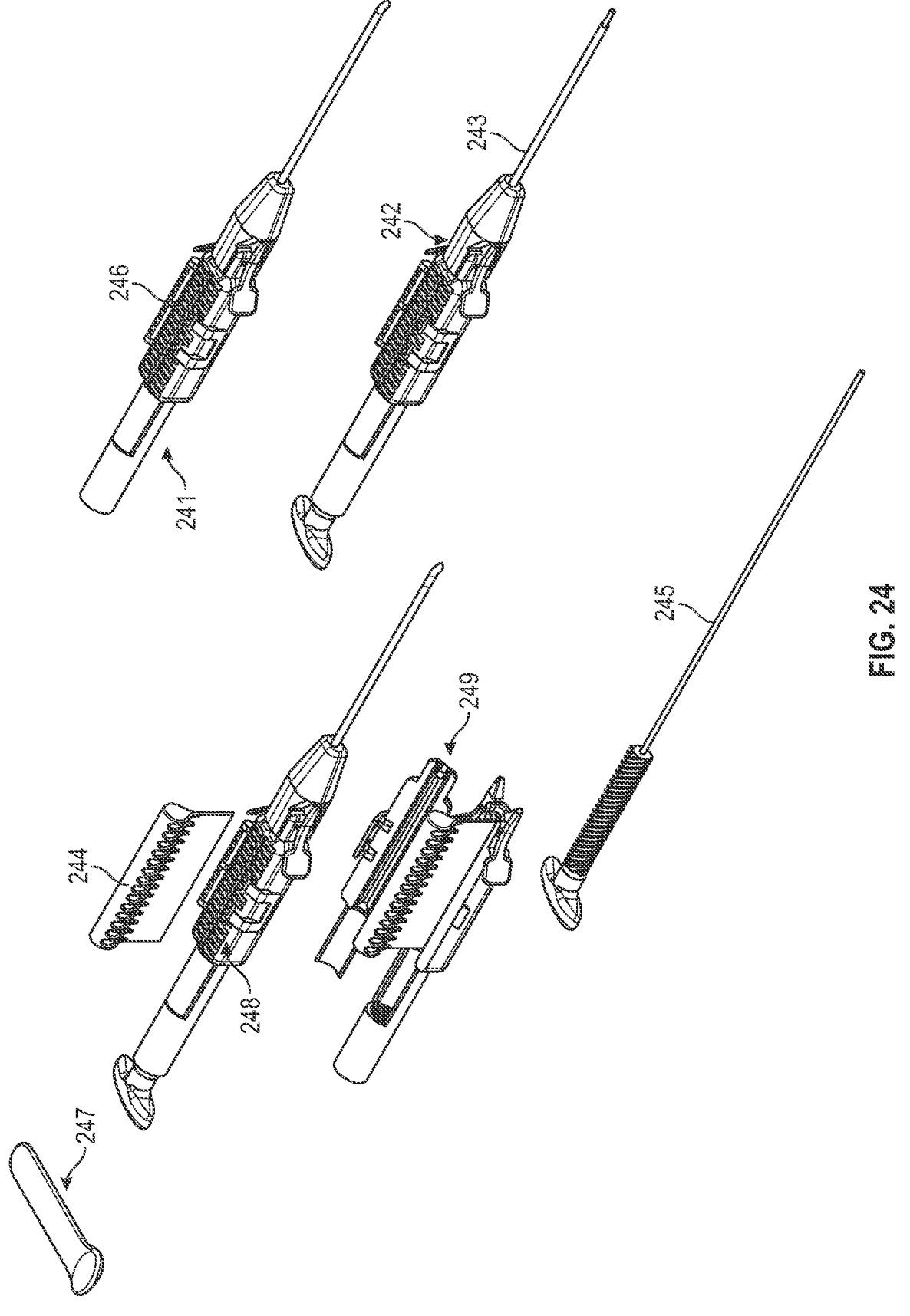
FIG. 24 schematically shows a perspective view of a bone delivery device including a cartridge having a single delivery channel loaded with a pack tool according to the present disclosure.

FIG. 24 schematically shows a perspective view of a bone delivery device 241 including a cartridge 242 having a single delivery channel 248 loaded with a pack tool 244. Bone delivery device 241 may include a cannula 243, plunger 245, and grip feature 246 similar to cannula 83, plunger 85, and grip feature 86 of bone delivery device 81. In some embodiments, the bone delivery device 241 includes a lid 249 hingeably connected to the cartridge 242. In some embodiments, the delivery channel 248 is situated within the lid 249. In such embodiments, the channel 248 is filled with bone graft material, then the lid 249 is secured to the cartridge 242 before the cartridge 242 is connected to the cannula 243 for delivery for the bone graft material.

Figure 26B:
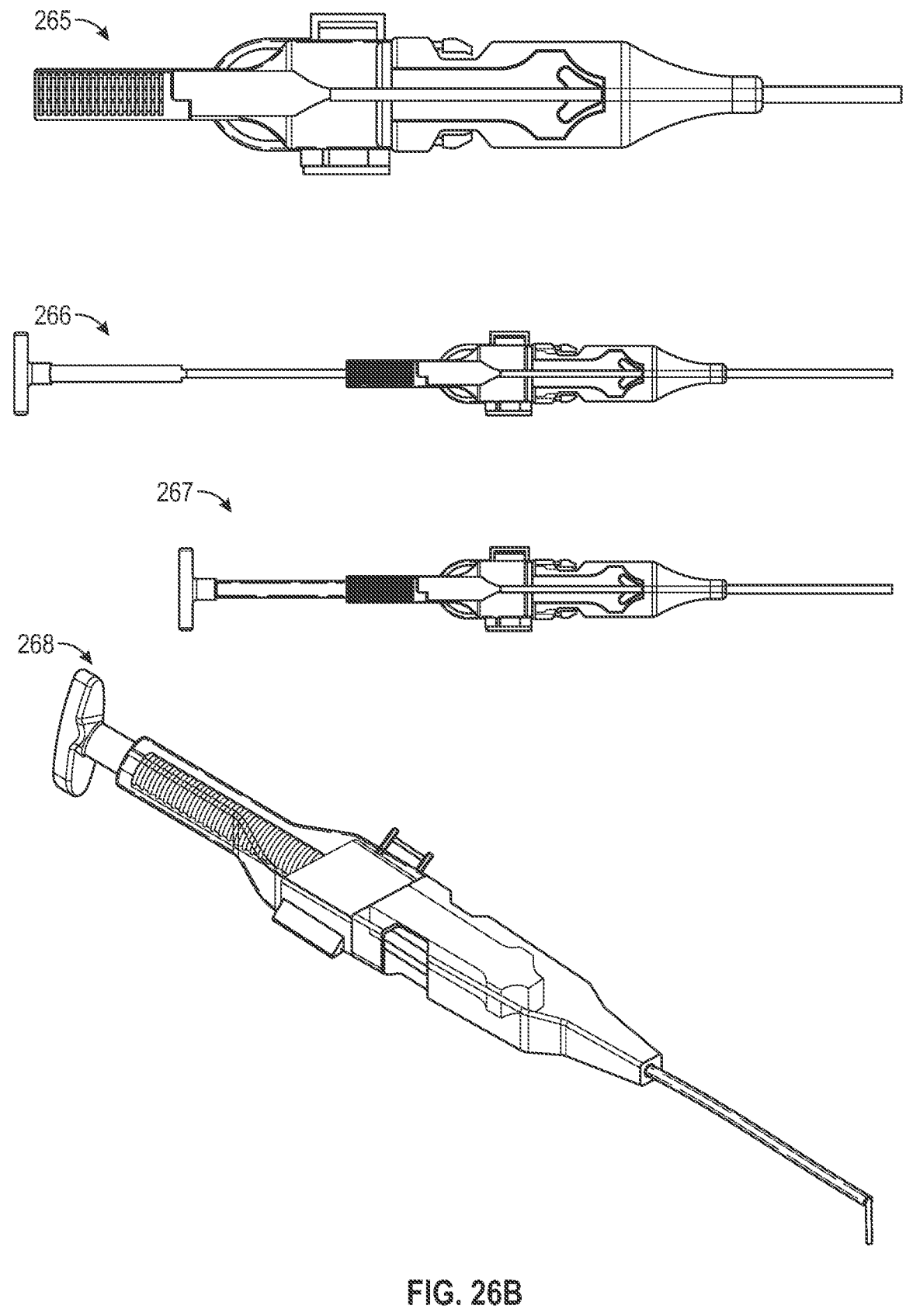

As discussed in more detail with regards to FIGS. 26A and 26B, bone material may be loaded into the delivery channel 248 with a bone scoop tool 247. The loaded bone material is then compacted with a pack tool 244.

The pack tool may also be used in conjunction with a multi-channel bone delivery device, such as device 1. For example, a user may add a measured amount of bone material to one or more channels of the device with the bone scoop tool, then pack the material into the channels with the pack tool. Then the lid of the device is added to the cartridge to enclose the channels. Then the material can be actuated through a cannula as described above.

FIG. 25 schematically shows a perspective view of a bone delivery device 251 including a cartridge 252 having a single delivery channel 258 and a hinged lid 259. Bone delivery device 251 may include a grip feature 256 similar to grip feature 86 of bone delivery device 81. The cartridge 252 may include a hinge connecting the lid 259 to a base 257. Bone delivery device 251 includes a plunger 255 that may be structurally similar to plunger 5 of bone delivery device 81, but further includes threading around a rod of the plunger 255. The cartridge 252 includes mated threading to enable controlled deployment of bone graft material. Once the threads of the plunger 255 engage the cartridge 252, the user may be required to twist the plunger 255 to continue expelling bone graft material out of the cannula 253, providing the user with more control over the rate and volume of expelled bone graft material.

In some embodiments, to ease the process of loading the bone material, portions of the cartridge 252 may be colored or textured to visual or tactically indicate the delivery channel 258. For example, FIG. 25 depicts a portion of the base 257 that may be colored opaque if the delivery channel 258 is transparent. Additionally or alternatively, portions of the cartridge 252 may include indicia such as words and/or reference lines to indicate where to load bone material.

FIGS. 26A and 26B schematically show a method of loading bone material into the bone delivery device of FIG. 25. The red area in each image represents the bone material. The method begins at Step 261, a user using a bone scoop tool to measure an amount of bone material that will fit in a delivery channel. The user then transfers the material from the bone scoop tool into the delivery channel.

In Step 262, the user selects a packing tool to compress the bone material in the delivery channel. In Step 263, the user compresses the material within the delivery channel of a cartridge. The cartridge may include a lid connected to a base by a hinge. In Step 264, the user closes the cartridge by moving the lid onto the base.

In Step 265, the user connects the cartridge to a delivery cannula. In some embodiments, the cartridge and the cannula may be connected by a dual clip. The dual clip reduces the possibility of the user unintentionally disconnecting the cartridge and cannula during later steps. The cannula may be at least partially transparent or translucent to allow the user to see the bone material. For example, the cannula may include a transparent or translucent sheath.

In Step 266, the user inserts a plunger into the cartridge to advance the bone material from the cartridge into the cannula. The internal diameter of the cannula is smaller than the diameter of the delivery channel within the cartridge. In Step 267, the plunger is advanced until a threaded portion of the plunger engages a threaded portion of the cartridge. At this point, the plunger cannot be advanced further without twisting the plunger. In Step 268, the user twists the plunger, causing the bone material to exit an aperture of the cannula. Advancement of the plunger can be stopped and started as needed to titrate a desired amount of bone material into an orthopaedic surgical site.

Figure 27A:
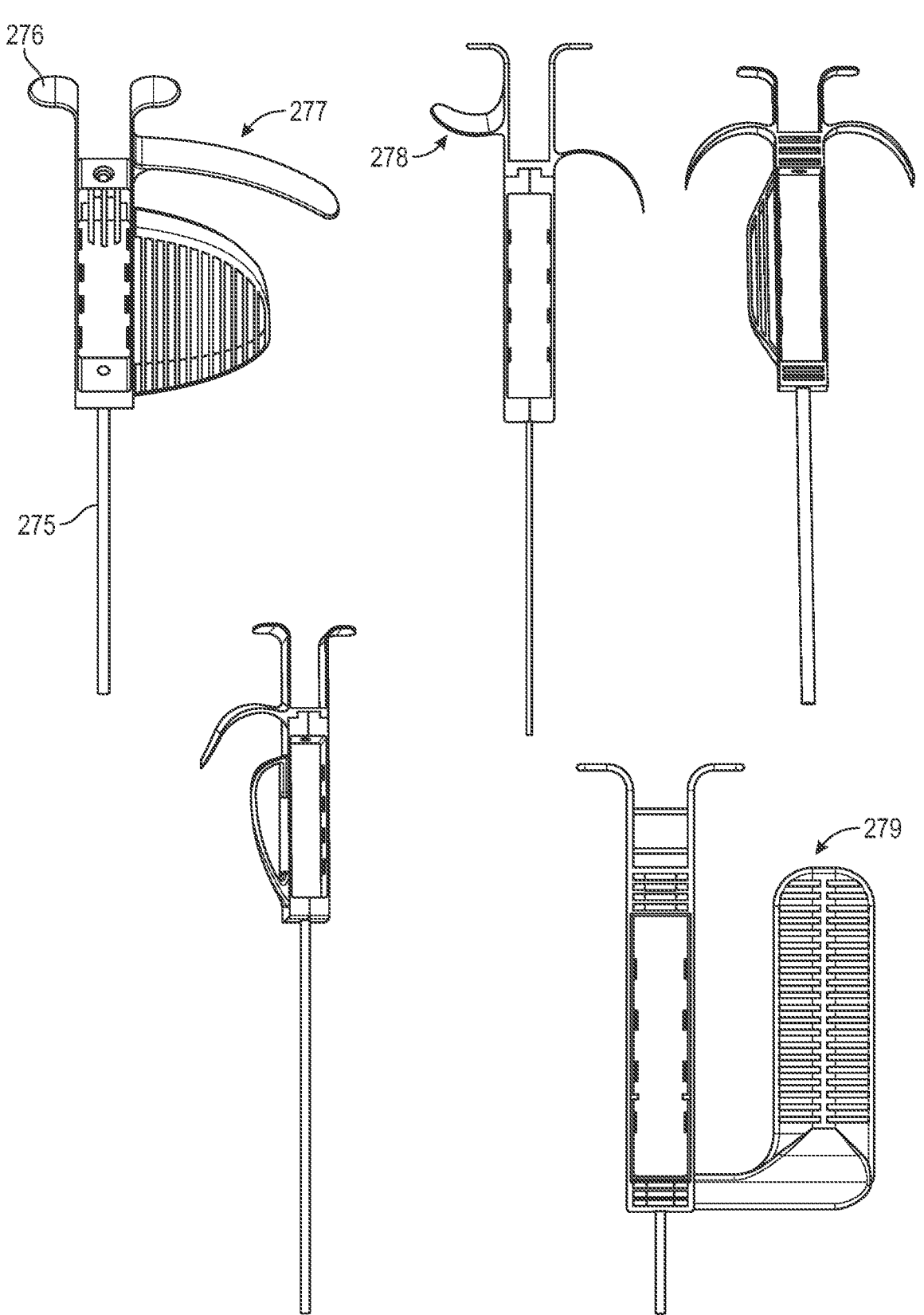

FIGS. 27A and 27B schematically show variations of hand grips 277 located on a bone delivery device 275. The hand grip 277 may be integrated as part of the frame of the device 275. In some embodiments, the hand grip 277 protrudes laterally from the frame. The hand grip 277 may be fashioned from the same material as the frame. The hand grip 277 may include a tactile surface 279 to improve a user's grip on the hand grip 277. Hand grip 277 may be included in the delivery devices discussed above, for example device 1.

The device 275 may also include one or more flanges 276 extending from a proximal end of the device 275. The flanges 276 are shaping for a syringing grip on a plunger that can be inserted into the frame. An opposing flange 277 may be situated under a flange 276 and be configured for a user to rest their thumb.

The proximal end of the device 275 may also include plunger rod lead-in feature 280. The feature 280 may be a conically shaped structure extending from the proximal end into a delivery channel within the device 275.

Figure 28:
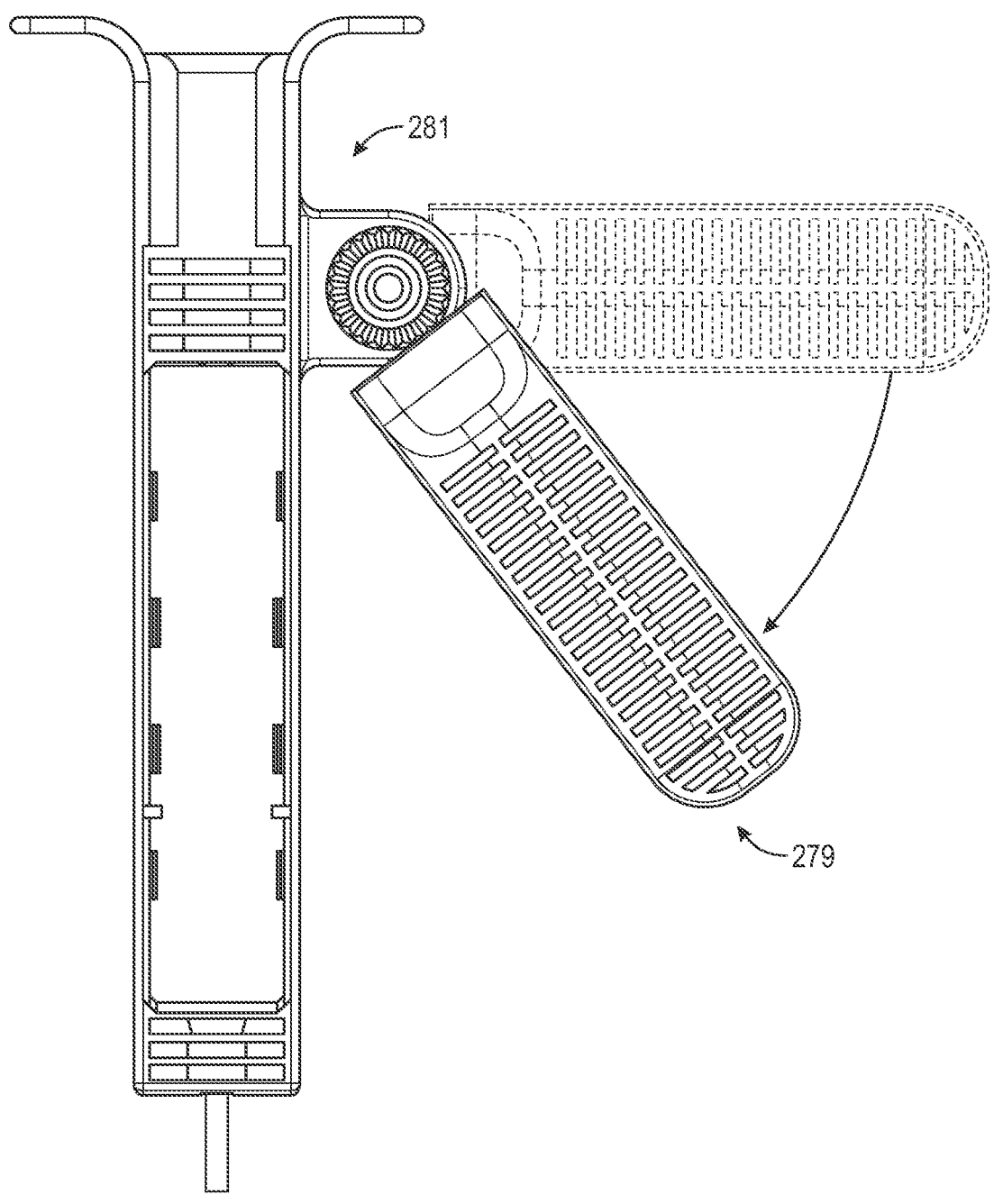
FIG. 28 schematically shows an adjustable joint facilitating movement of a hand grip.

FIG. 28 schematically shows an adjustable joint 281 facilitating movement of a hand grip 277. The joint 281 allows for movement of the hand grip 277 either towards, or away from, the frame of the device 275. The joint 281 may be located at a proximal end of the hand grip 277 and adjacent to the frame.

In some embodiments, the bone material may be mixed with saline, BMA (bone marrow aspirate), and/or other bone carrier products to create a more lubricious bone material that is easier to advance though a cannula. Highly crystalline polymers (such as PTFE) may be added to the components of the bone delivery device to increase the lubriciousness of the surface of the delivery channels and delivery cannula. In some embodiments, the delivery channels and delivery cannula may be filled with a lubricious mixture of BMA and saline before bone material is loaded into the device.

In some embodiments, the bone material may be morselized until the bone material forms a uniform slurry. For example, the bone material may be passed through a series of blades to facilitate the morselization process.

In some embodiments, the bone delivery device may be vibrated during delivery of the bone material to prevent adhesion of the bone material to the walls of the delivery channels and delivery cannula.

In some embodiments, the delivery channels and/or delivery cannula may include a liner. For example, a liner could include a layer of silicone. In some embodiments, the liner may be flexible. In some embodiments, the liner may be configured to move with the bone material out of the cannula. For example, the liner may include one or more wires or a thin polyurethane film.

In some embodiments, the bone material may be preloaded onto the plunger so that bone material is supported on multiple surfaces as the bone material is being advanced through a cannula, reducing the compaction force experienced by the bone material at the proximal end of the delivery channel or cannula, reducing the material's tendency to buckle and grab onto the surfaces of the delivery channel and delivery cannula. Alternatively, the plunger may be removed from the interior surface of the delivery channel creating a hollow interior that the bone could collapse down into if the material hit pockets of friction.

The Figures depict devices including a straight cannula, however the cannula can feature a 'ramp' or a bullet nose tip that is blunt and has an angled ramp to guide bone material delivery at an angle between 1-90 degrees. This feature can be merged with any of the aforementioned concepts. The delivery cannula can also be curved in conjunction with a plunger that can follow the curve.

A bone delivery device can include a cannula having a first diameter and a cartridge in fluid communication with the cannula. The cartridge can include a base containing one or more delivery channels configured to receive bone material and a lid comprising one or more protrusions configured to compact the bone material within the one or more delivery channels. After compaction, a different lid that does not contain a protrusion replaces the compaction lid for delivery. The delivery lid maintains a clearance between the compacted bone and the lid. An alternate embodiment does not have a compaction lid step or component; in this alternate embodiment, the delivery cartridge has one or more channels that maintain a diameter smaller than the delivery cannula. The user compresses bone into the channel below a reference line that maintains a smaller diameter of bone relative to the diameter formed upon closing delivery lid. This diameter is smaller than the diameter of the delivery cannula. Precision delivery can be achieved with a threaded plunger to titrate the bone delivery. The bone material is compacted to a second diameter smaller than the first diameter.

A method of delivering bone can include selecting a bone delivery device, the device including a cannula having a first diameter and a cartridge in fluid communication with the cannula, the cartridge including a base containing one or more delivery channels configured to receive bone material, inserting the bone material into the one or more delivery channels, compacting the bone material by using a pack tool or other instrument to compress bone into the channels such that the diameter of compressed bone is smaller than the diameter of the delivery channel with closed graft cartridge lid. The delivery channel diameter is smaller than the delivery cannula. Compression can also be performed with an alternate embodiment including a compression lid with protrusions to pack down bone material to aforementioned diameter that is smaller than the diameter of the delivery channel.

Although the present disclosure has been described with reference to exemplary embodiments and implementations, the present disclosure is not limited by or to such exemplary embodiments/implementations. Rather, the present disclosure is susceptible to revision, modification and/or refinement without departing from the spirit or scope hereof.

We claim:

1. A bone delivery device, comprising;
a cannula defining a first diameter;
a frame extending from a proximal end of the cannula, the frame including a side opening; and
a cartridge comprising a plurality of delivery channels therein that define second diameters smaller than the first diameter, each delivery channel configured to receive bone material, wherein the cartridge is insertable into the frame through the side opening and slidable laterally through the side opening for moving the cartridge to any one of a plurality of delivery positions within the frame that each correspond to one of the plurality of delivery channels in the cartridge so that, via said moving, a user can separately longitudinally align each of the plurality of delivery channels with the cannula so as to be in fluid communication with the cannula for advancing the bone material from the respective delivery channel into the cannula.

2. The bone delivery device of claim 1, wherein an outer surface of the cartridge includes a grip feature comprising a tactile surface.

3. The bone delivery device of claim 1, wherein the first diameter ranges from 1 mm to 12 mm.

4. The bone delivery device of claim 3, wherein the first diameter ranges from 3 mm to 6 mm.

5. The bone delivery device of claim 1, wherein the plurality of delivery channels are non-parallel with one another in the cartridge.

6. The bone delivery device of claim 1, wherein the cartridge includes a base and a lid that combine to form the plurality of delivery channels.

7. The bone delivery device of claim 6, wherein the plurality of delivery channels each include a chamfered edge formed in the base.

8. A bone delivery device, comprising;
a cannula including an open distal end through which a bone material can travel to exit the bone delivery device;
a frame extending from a proximal end of the cannula, the frame including a side opening; and
a cartridge including a plurality of longitudinal delivery channels therein for receiving the bone material, the cartridge insertable into the frame through the side opening, the cartridge further slidable laterally through the side opening for moving the cartridge to any one of a plurality of delivery positions within the frame that each correspond to one of the plurality of longitudinal delivery channels in the cartridge so that, via said moving, a user can separately longitudinally align each of the plurality of longitudinal delivery channels with the cannula so as to be in fluid communication with the cannula for advancing the bone material from the respective longitudinal delivery channel into the cannula.

9. The bone delivery device of claim 8, wherein the plurality of longitudinal delivery channels are non-parallel with one another in the cartridge.

10. The bone delivery device of claim 8, wherein the cartridge includes a base and a lid that combine to form the plurality of longitudinal delivery channels.

11. The bone delivery device of claim 10, wherein the plurality of longitudinal delivery channels each include a chamfered longitudinal edge formed in the base.

12. The bone delivery device of claim 8, wherein the cannula has a first diameter, and wherein each of the plurality of longitudinal delivery channels has a second diameter smaller than the first diameter.

13. The bone delivery device of claim 12, wherein the first diameter is less than 6 mm.

14. The bone delivery device of claim 8, wherein the cannula has a first diameter ranging from 1 mm to 12 mm.

15. The bone delivery device of claim 14, wherein the first diameter ranges from 3 mm to 6 mm.

* * * * *